United States Patent
Silveri et al.

(10) Patent No.: US 6,238,555 B1
(45) Date of Patent: May 29, 2001

(54) AMPEROMETRIC HALOGEN CONTROL SYSTEM

(75) Inventors: Michael A. Silveri, Incline Village, NV (US); Emil Milosavljevic, Lakewood, CO (US); Caba Calic, Reno, NV (US)

(73) Assignee: BioQuest, Reno, NV (US)

( * ) Notice: Subject to any disclaimer, the term of this patent is extended or adjusted under 35 U.S.C. 154(b) by 0 days.

(21) Appl. No.: 09/187,241

(22) Filed: Nov. 6, 1998

Related U.S. Application Data

(60) Provisional application No. 60/064,899, filed on Nov. 7, 1997, and provisional application No. 60/075,276, filed on Feb. 19, 1998.

(51) Int. Cl.[7] .............................. B01D 21/30; C02F 1/76
(52) U.S. Cl. ...................... 210/143; 210/169; 210/192; 210/243
(58) Field of Search .................... 210/143, 192, 210/198.1, 243, 169, 96.1; 204/228.6

(56) References Cited

U.S. PATENT DOCUMENTS

| | | | |
|---|---|---|---|
| 3,092,566 | 6/1963 | Negus | 204/240 |
| 3,305,472 | 2/1967 | Oldershaw et al. | 204/268 |
| 3,351,542 | 11/1967 | Oldershaw et al. | 204/149 |
| 3,361,663 | 1/1968 | Murray et al. | 204/278 |
| 3,458,414 | 7/1969 | Crane et al. | 204/149 |
| 3,926,754 | 12/1975 | Lee | 204/152 |
| 3,959,087 | 5/1976 | Morrow . | |
| 4,028,197 | 6/1977 | Capuano . | |
| 4,033,830 | 7/1977 | Fletcher, III | 205/775 |
| 4,033,871 * | 7/1977 | Wall | 210/143 |

(List continued on next page.)

FOREIGN PATENT DOCUMENTS

| | | |
|---|---|---|
| 0 133 920 A1 | 3/1985 | (EP) . |
| 0 283 962 | 9/1988 | (EP) . |
| 0 320 109 | 6/1989 | (EP) . |
| 0 343 092 A1 | 11/1989 | (EP) . |
| 0 537 528 A1 | 4/1993 | (EP) . |
| 2 469 708 | 5/1981 | (FR) . |
| WO 90 10734 | 9/1990 | (WO) . |
| WO 96 30307 | 10/1996 | (WO) . |

OTHER PUBLICATIONS

The Halogen System brochure, printed Nov. 1990.
Huang, H. et al., "A Pulse Amperometric Sensor for the Measurement of Atmospheric Hydrogen Peroxide," Analytical Chemistry, vol. 68, No. 13, dated Jul. 1, 1996, pp. 2062–2066.
Jandik, P. et al., CRC Critical Reviews in Analytical Chemistry, vol. 20, Issue 1, (1988), pp. 1–74.
Lunte, C., University of Kansas, "Voltammetric Detection for Liquid Chromatography,"LC–GC, vol. 7, No. 6, pp. 492–494, (Undated).

Primary Examiner—David A. Simmons
Assistant Examiner—Frank M. Lawrence
(74) Attorney, Agent, or Firm—Knobbe, Martens, Olson & Bear, LLP

(57) ABSTRACT

An amperometric bromine control system accurately maintains a desired concentration of bromine within a home spa or in other water features. The control system employs amperometric sensing to measure the bromine concentration in the spa water and uses this measurement to control the electrochemical production of bromine through the oxidation of aqueous bromide. The level of bromide in the spa water desirably is greater than 50 ppm in order to obtain a linear relationship between the current level sensed through the amperometic measurement and the concentration level of bromine in the water. In this manner, the control system can accurately measure the bromine concentration in the spa water and precisely maintain the bromine concentration within a desired range between about 2 ppm and 6 ppm.

82 Claims, 20 Drawing Sheets

U.S. PATENT DOCUMENTS

| | | | |
|---|---|---|---|
| 4,129,479 | 12/1978 | Morrow | 204/229.7 |
| 4,129,493 | 12/1978 | Tighe et al. | 205/780 |
| 4,225,410 | 9/1980 | Pace | 204/195 R |
| 4,440,603 | 4/1984 | VanEffen et al. | 204/400 |
| 4,496,454 | 1/1985 | Berger | 204/402 |
| 4,657,670 | 4/1987 | Newton | 210/139 |
| 4,767,511 | 8/1988 | Aragon | 210/746 |
| 4,917,774 | 4/1990 | Fisher | 204/153.1 |
| 4,992,156 | 2/1991 | Silveri | 204/237 |
| 5,221,444 | 6/1993 | Silveri | 204/237 |
| 5,254,226 | 10/1993 | Williams et al. | 210/748 |
| 5,268,092 | 12/1993 | Eden | 210/198.1 |
| 5,326,443 | 7/1994 | Hilbig | 204/237 |
| 5,328,574 | 7/1994 | Mercier | 204/272 |
| 5,368,706 | 11/1994 | Bowers et al. | 204/291 |
| 5,398,711 | 3/1995 | Ardrey, Jr. | 137/343 |
| 5,403,451 | 4/1995 | Riviello et al. | 204/153.1 |
| 5,422,014 | 6/1995 | Allen et al. | 210/743 |
| 5,425,869 | 6/1995 | Noding et al. | 204/418 |
| 5,499,197 | 3/1996 | Fou | 210/143 |
| 5,509,410 | 4/1996 | Hill et al. | 128/637 |
| 5,518,602 | 5/1996 | Kessel | 204/415 |
| 5,545,310 | 8/1996 | Silveri | 205/537 |

\* cited by examiner

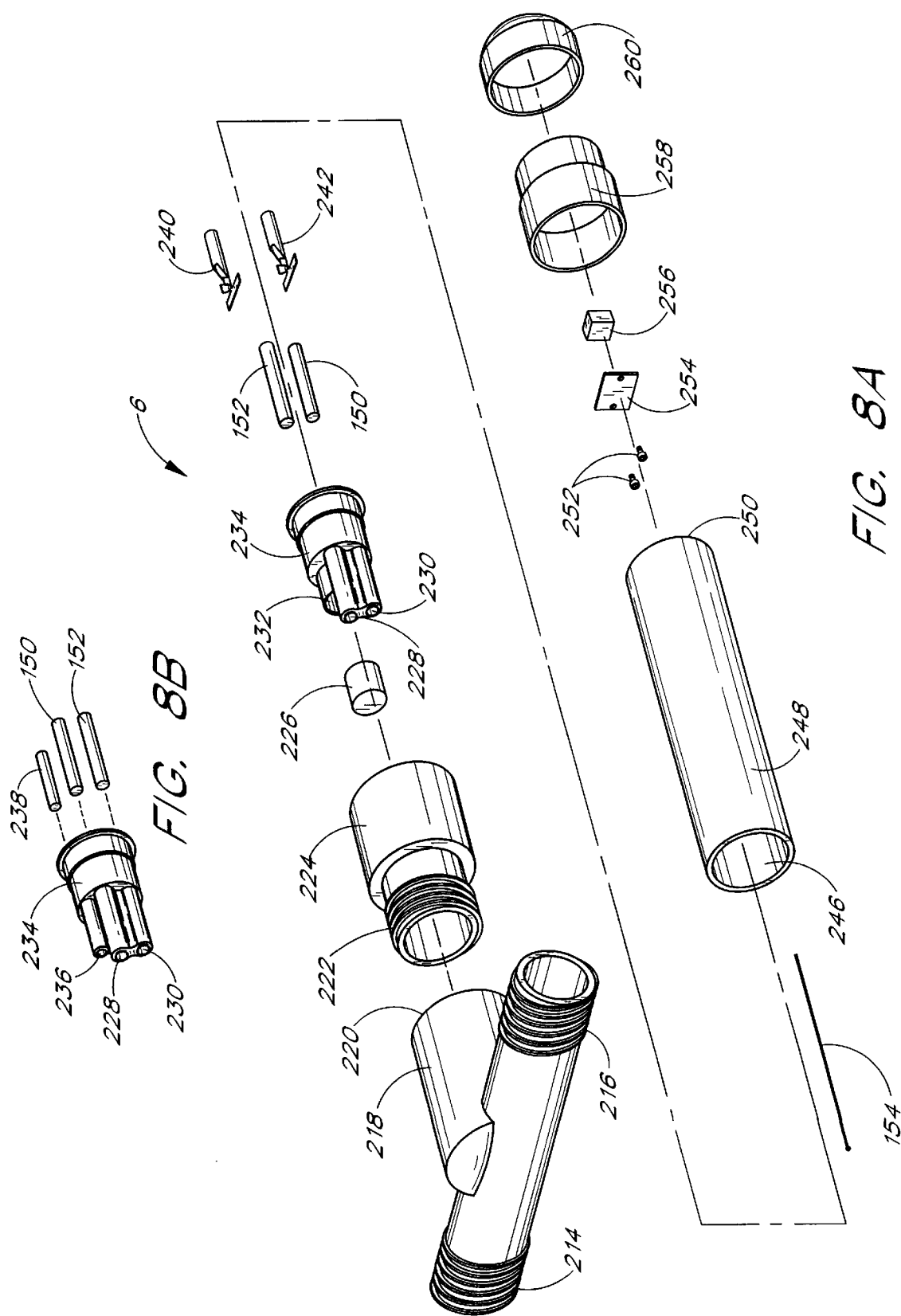

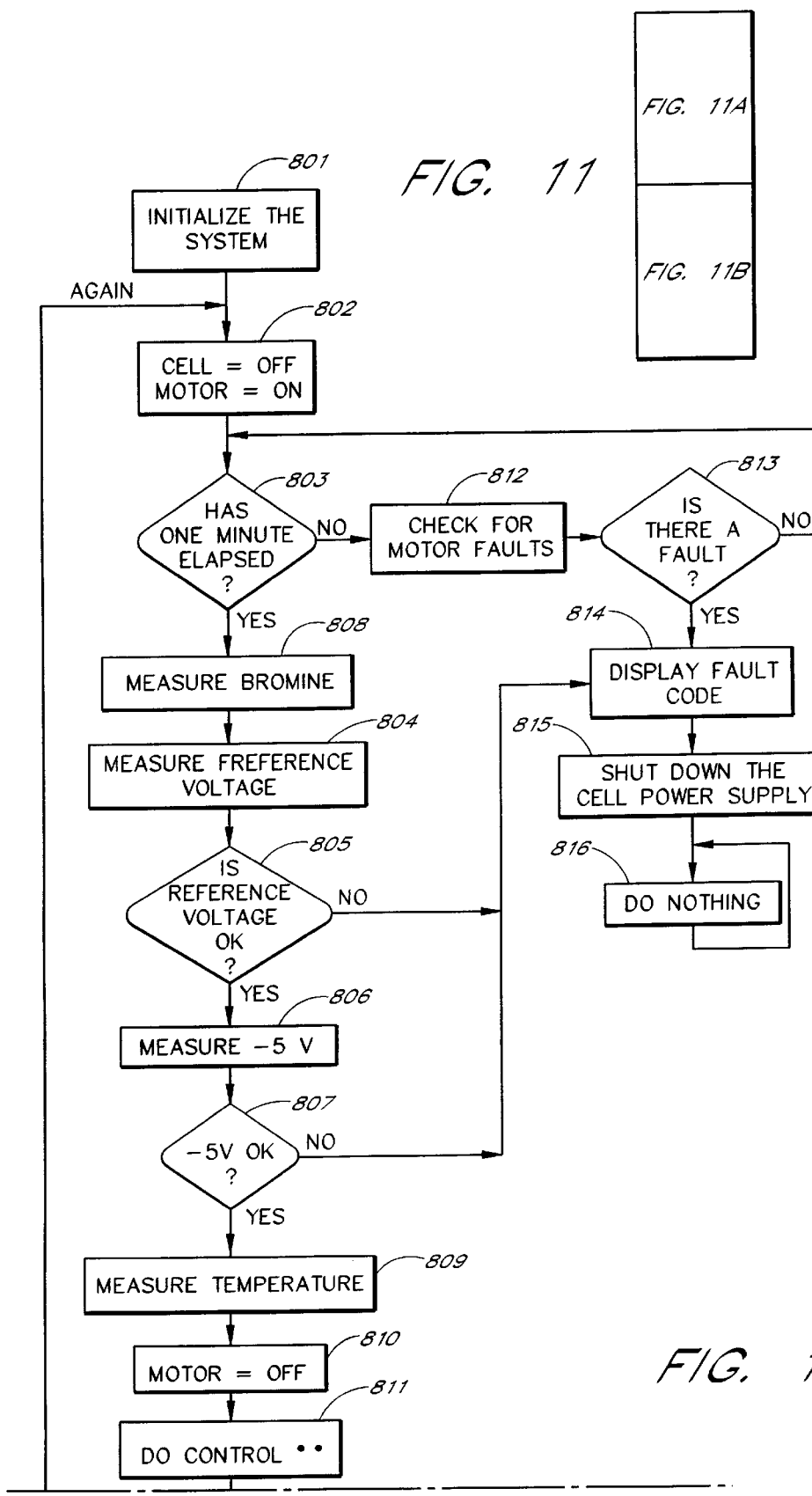

AMPEROMETRIC HALOGEN CONTROL SYSTEM

RELATED CASES

This application claims the benefit of priority under 35 U.S.C. §119(e) of provisional U.S. Application Serial No. 60/064,899, filed on Nov. 7, 1997, and of provisional U.S. Application Serial No. 60/075,276, filed on Feb. 19, 1998.

BACKGROUND OF THE INVENTION

1. Field of the Invention

The present invention relates to a water purification system, and more particularly to an automatic sanitizing system and a method for maintaining in a water feature a sanitizing agent concentration within a desired range.

2. Description of Related Art

Portable self-contained spas have become popular in recent years. Such spas are easy installed and powered by existing electrical lines or dedicated electrical hook-ups.

Once installed, the homeowner must sanitize the spa to prevent the proliferation of disease-causing microorganisms. Typical spa maintenance requires adding granular sodium dichloro-isocyanurate as a sanitizing agent to control such bacteria growth. Bromine alternatively can be added as a sanitizing agent. Bromine preferably is used as the sanitizing agent in the spa because it remains in liquid form at 100° F., unlike chlorine.

Many spa owners today, however, do not properly maintain their spas. Some owners do not adequately sanitize their spas despite the danger of unhealthy bacteria growth. Other owners over-sanitize their spas which can damage spa equipment, including the heater and the spa shell.

In an effort to ease spa maintenance so as to avoid both under- and over-sanitizing, some prior systems have automated at least part of the maintenance. For example, an automatic demand chlorination system is disclosed in U.S. Pat. No. 4,657,670 for use with a recirculation unit for a swimming pool. The automatic demand chlorination system has a dry chlorinator which feeds chlorine into the water if a chlorine need is detected by a sensing unit. An oxidation-reduction type sensor is used in the automated system for this purpose. Although oxidation-reduction type sensors have been used to measure the concentration of halogens used as sanitizing agents in water features there are some limitations, e.g., a nonlinear response to variations of halogen concentration or a required calibration to changing starting points.

SUMMARY OF THE INVENTION

In view of the deficiencies associated with prior solutions to maintain a desired concentration of a sanitizing agent and thereby to maintain a certain hygienic condition in spa water, there exists a need to improve accuracy, reliability and practicability of halogen measurements in a water feature, e.g., a spa, pool, fountain, cooling tower and the like.

In accordance with an aspect of the present invention a combination of a water feature filled with water containing a sanitizing agent and an automatic sanitizing system is provided. The automatic sanitizing system comprises a sanitizing agent generator communicating with the water feature, and an amperometric sensor that includes a probe positioned in contact with water. The sensor generates an output signal indicative of the concentration of sanitizing agent in the water. The automatic sanitizing system further comprises a control system that receives the signal from the sensor and operates the generator at least between an active state and an inactive state depending on the concentration of the sanitizing agent in the water. In this manner, the concentration of the sanitizing agent in the water is automatically maintained within a preset range.

A further aspect of the present invention involves an automatic sanitizing system. The automatic sanitizing system comprises an electrolytic cell for emersion in water and an amperometric sensor probe positionable in contact with the water. The sensor probe generates an output signal indicative of a concentration of a chemical species in the water. The automatic sanitizing system further comprises a control system connected to the sensor probe to receive the output signal. The control system is connected to the electrolytic cell to operate the electrolytic cell at least between active and inactive states depending on the concentration of the chemical species in the water.

A further aspect of the present invention involves a system comprising a controller device, a feedback circuitry, a controlled device and a power supply unit. Additionally, the system comprises an isolator which electrically isolates the controller device at least from the power supply unit and the controlled device.

Another aspect of the present invention involves an automatic sanitizing system. The automatic sanitizing system comprises an electrolytic cell for emersion in water and an amperometric sensor probe positionable in contact with the water. The sensor probe generates an output signal indicative of a concentration of a chemical species in the water. The automatic sanitizing system further comprises a control system connected to the sensor probe to receive the output signal. The control system is connected to the electrolytic cell to operate the electrolytic cell at least between active and inactive states depending on the concentration of the chemical species in the water. Furthermore, the automatic sanitizing system comprises means for electrically isolating the control system from the power supply unit.

An additional aspect of the present invention involves a combination of a water feature filled with water containing an electrolyte prepared by the step of adding a salt composition to the water, and an automatic sanitizing system. The salt composition comprises at least about 50 ppm sodium bromide and at least about 500 ppm sodium chloride. The automatic sanitizing system comprises a sanitizing agent source communicating with the water feature, an amperometric sensor including a probe, and a control system receiving a sensor signal and operating the sanitizing agent source at least between an active state and an inactive state. The sanitizing agent source includes a sanitizing agent generator or a dispenser containing the sanitizing agent.

A further aspect of the present invention involves an automatic sanitizing system. The automatic sanitizing system comprises a sanitizing agent source, an amperometric sensor including a probe, and a control system including v microcontroller. The amperometric sensor includes a potentiostat for amperometric measurements which comprises a plurality of operational amplifiers, each is provided with an asymmetrical power supply by an operational amplifier sub-power supple Another aspect of the present invention involves a combination of a v feature containing water, and an amperometric sensor probe in contact with the, for sensing the sanitizing agent in the water feature. The amperometric sensor comprises a housing, a working electrode and a counter electrode. Each electrode has a portion which is exposed relative to the housing at a working end. The amperometric sensor probe further comprise a reference electrode immersed in an electrolyte and positioned within the housing. A junction is arranged between the electrolyte and an exterior and the electrolyte. In an embodiment of the present invention, the exposed portions of the working and counter electrodes lie adjacent to each other and comprise carbon-like material.

A still further aspect of the present invention involves an amperometric sensor probe. The probe comprises a housing and three electrodes lie adjacent to counter electrode and a reference electrode. The working electrode and the counter electrode each have a portion which is exposed relative to the housing at a working end. The reference electrode is immersed in an electrolyte and is positioned within the housing. A junction, which is arranged between the electrolyte and the exterior of the working ends, allows ionic communication between the working ends exterior and the electrolyte. The probe further comprises a memory device that stores data specific for the probe. The memory device is connected to a data port that is also connected to three electrodes.

A further aspect of the present invention involves a method of cleaning a first electrode of a probe, with the probe including at least the first electrode and a second electrode. The method comprising applying a sequence of three different references voltages between said first and second electrodes.

An additional aspect of the present invention involves a method for automatically maintaining the concentration of a sanitizing agent in a water feature within a desired range using an automatic sanitizing system. The method comprising the steps of providing an aqueous solution with a sanitizing agent in the water feature; providing an amperometric sensor probe including at least a reference electrode and a working electrode; placing at least a portion of the working electrode in contact with the aqueous solution; maintaining a generally constant voltage between the electrodes; measuring a current through the working electrode which is indicative of the concentration of the sanitizing agent within the aqueous solution; and using the measured current to maintain the concentration of the sanitizing agent in the aqueous solution within the preset range.

Another aspect of the present invention involves a method for automatically maintaining the concentration of bromine in a water feature within a preset range. The method comprises the steps of providing an aqueous solution with a bromide concentration of at least about 50 ppm in the water feature. Elemental bromine is electrochemically or chemically produced in the aqueous solution and the concentration of elemental bromine in the aqueous solution is measured. The measured bromine concentration is used to control the production of bromine to maintain a concentration of elemental bromine in the aqueous solution within the preset range. In an embodiment of the present invention, the concentration of elemental bromine in the aqueous solution is maintained within the range of about 2 to about 6 parts per million (ppm). The production of bromine desirably occurs at a rate of about 1 to 2 grams per hour.

An additional aspect of the present invention involves a method for determining a measurement characteristic of a sensor probe. The method comprises the acts of providing a sensor probe with a memory device, placing the sensor probe into a known environment, determining a measurement characteristic of the sensor probe when placed into said known environment, and storing in said memory device the measurement characteristic of the sensor probe.

Water features, especially spas and pools also suffer from high transient activity causing changing hygienic conditions. A still further aspect of the invention is therefore, to sense water feature usage activity and to initiate production of more sanitizing agent when usage is detected rather than to wait until the concentration of the sanitizing agent drops.

Further aspects, features, and advantages of the present invention will become apparent from the detailed description of the preferred embodiment which follows.

BRIEF DESCRIPTION OF THE DRAWINGS

The above-mentioned and other features of the invention will now be described with reference to the drawings of a preferred embodiment of the present automatic sanitizing system. The illustrated embodiment is intended to illustrate, but not to limit the invention. The drawings contain the following figures:

FIG. 8A is an exploded view of a sensor probe in accordance with a preferred embodiment of the present invention;

FIG. 8B is an exploded view of an end cap and electrodes configured in accordance with another preferred embodiment which can be used with the basic structure of the sensor probe illustrated in FIG. 8A;

FIG. 11, comprising FIGS. 11A and 11B, is a flowchart illustrating the operation of the automatic sanitizing system in accordance with a preferred embodiment of the present invention;

DETAILED DESCRIPTION OF THE PREFERRED EMBODIMENT

Figure 1A:
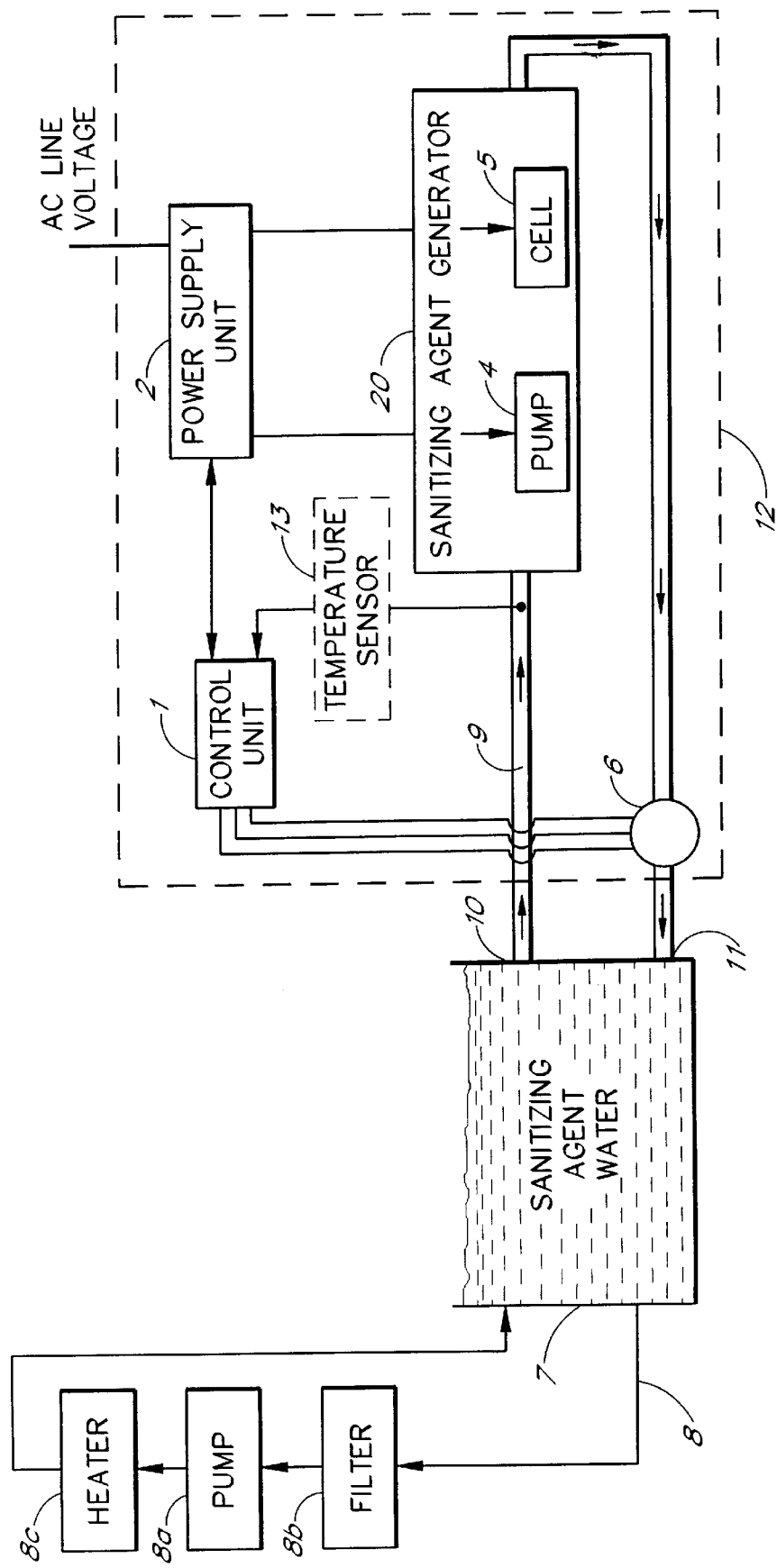
FIG. 1A is a schematic illustration of a combination of a water feature and an automatic sanitizing system in accordance with a preferred embodiment of the present invention.

FIG. 1A is a schematic illustration of a water feature 7 in combination with an automatic sanitizing system 12 which is configured in accordance with a preferred embodiment of the present invention. For the following description of the invention, the water feature 7 is illustrated and described as a spa, portable or built-in. The automatic sanitizing system 12, however, also can be used in other types of water features, such as, for example, but without limitation, swimming pools, water fountains, industrial cooling towers and the like.

A spa 7 is equipped with a conventional first water circulation line 8 comprising a pump system 8a for circulating spa water through the line 8, a filter 8b to extract leaves, bodily hair and/or other solid impurities from the water, and a water heating system 8c. The spa pump system 8a can include, for example, either a two-speed pump or the combination of a booster pump and a main pump; the pump system 8a circulates water through the line 8 at a low flow rate when operating under cleaning and/or heating modes, and circulates water through the line 8 at a high flow rate when operating under a user mode. The spa 7 also has several water jets which communicate with the circulation line 8 and can be activated together or individually by a user. When the pump system 8a operates in the user mode, these jets output water streams under high pressure generated by the pump system 8a.

A second water circulation line 9 is attached to and communicates with the spa 7 through two openings 10, 11. The second water circulation line 9 desirably works independently from the first water circulation line 8; however, the two circulation lines 8, 9 can also be integrated. In FIG. 1, however, the two water circulation lines 8, 9 are physically separated from and operate independent of each other.

The second water circulation line 9 is associated with the automatic sanitizing system 12. As indicated by arrows, spa water desirably flows within the water circulation line 9, entering the water circulation line 9 through the influent opening 10 and exiting the line 9 through the effluent opening 11 thereby creating a circulation loop.

The openings 10, 11 desirably are formed in a unitary fitting; however, the openings 10, 11 can be separately positioned at remote locates on the spa body relative to each other.

The sanitizing system 12 is disposed within the circulation loop formed by the water circulation line 9, and includes a sanitizing agent source. In the illustrated embodiment, the sanitizing agent source is a generator 20 that produces the sanitizing agent. The generator 20 is located within the water circulation line 9 and when activated desirably generates a halogen sanitizing agent or an intermediate in the reaction path leading to the halogen sanitizing agent.

A control unit 1 operates the generator 20 in accordance with spa water characteristics that are obtained from a sensing system which includes an amperometric sensor, and an optional temperature sensor 13 and a pH sensor. A probe 6 desirably functions as a combined sensor probe for the amperometric and pH sensors, as described below.

As illustrated in FIG. 1A, the sensor probe 6 is positioned within the water circulation line 9 to immerse at least a portion of the probe 6 within the water flow through the line 6. The sensor probe 6 desirably lies downstream of the generator 20. At this location, bacteria growth (e.g., algae growth) on the sensor probe 6 is minimized.

The temperature sensor 13 is illustrated with dashed lines to indicate that it is optional to include such a temperature sensor 13 in the sensing system. The temperature sensor 13 is also positioned within the water circulation line 9 so as to provide reliable readings of the water temperature. In the illustrated embodiment, the temperature sensor 13 is positioned upstream of the generator 20.

The control unit 1 is connected to the sensor probe 6, the temperature sensor 13 and a power supply unit 2. The power supply unit 2 desirably is connected to an external power line at a line voltage of either 120 volts or 240 volts.

In the illustrated embodiment, the control unit 1 and the power supply unit 2 are located near the generator 20, as well as near the sensor probe 6 and the temperature sensor 13. However, the control unit 1 and the power supply unit 2 can be remotely positioned relative to each other and relative to the sensor probe 6 and the temperature sensor 13.

As schematically represented in FIG. 1A, the generator 20 includes an electrolytic cell 5 and a pump 4 for circulating water through the water circulation line 9 and the electrolytic cell 5. The pump 4 and cell 5 desirably are integrated into a single housing, as described below. The pump 4 and the electrolytic cell 5, however, can be contained in different housings and located at different locations within the circulation line 9. However, it is understood that the electrolytic cell 5 can also be positioned directly in the water feature 7.

Figure 1B:
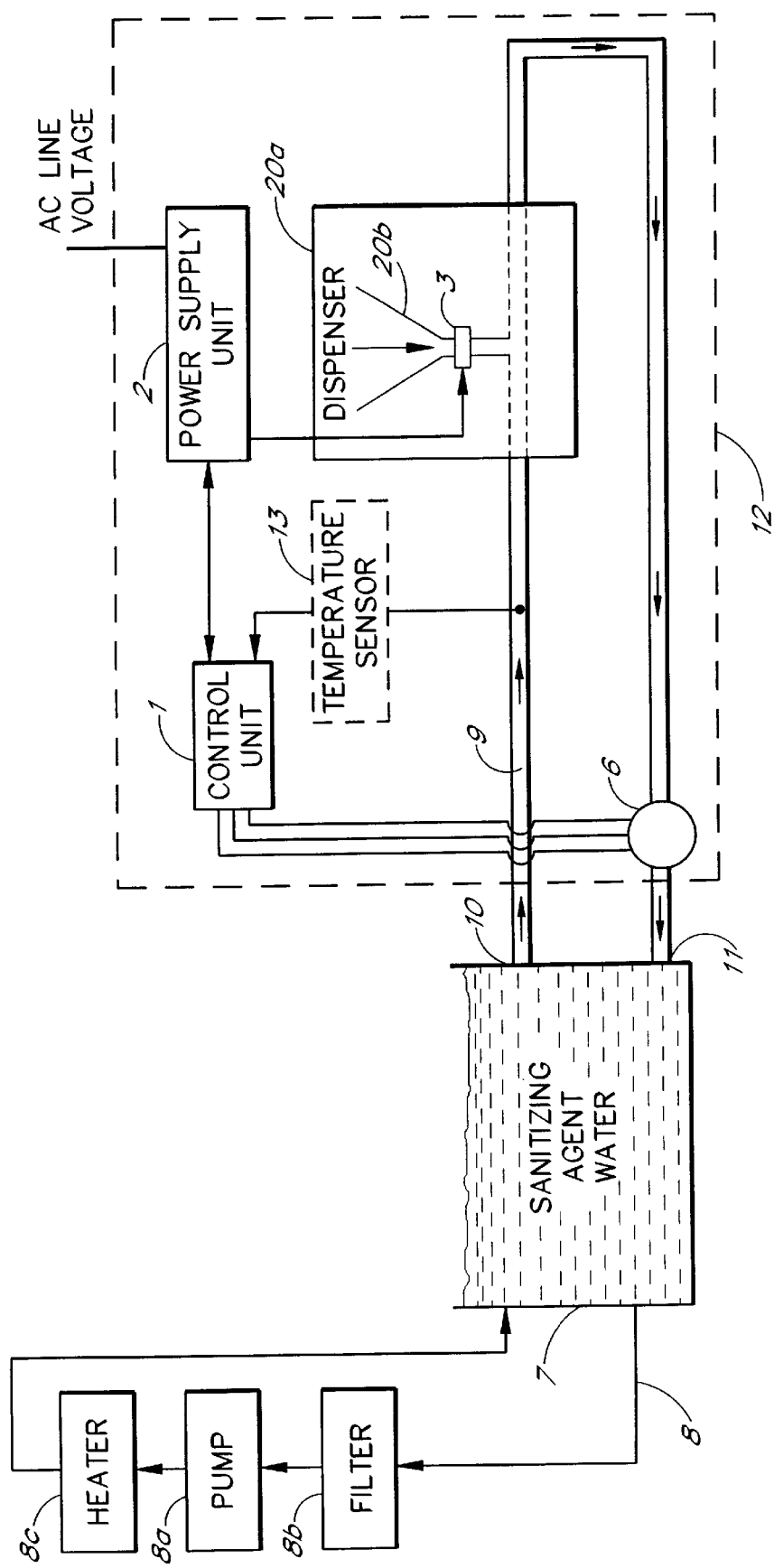
FIG. 1B is a schematic illustration of a combination of a water feature and an automatic sanitizing system in accordance with a further embodiment of the present invention.

FIG. 1B is a schematic illustration of another embodiment of the present invention. This embodiment is similar to the embodiment shown in FIG. 1A; same components therefore have been identified by the same reference numerals. In the illustrated embodiment, the sanitizing agent source is a dispenser 20a comprising a reservoir 20b for containing the sanitizing agent and a solenoid-controlled valve 3. An output of the valve 3 is connected to the water circulation line 9. Via the power supply unit 2, the control unit 1 selectively controls the flow of the sanitizing agent from the reservoir 20b into the water. The control unit 1 operates the valve 3 at least between an active and inactive state depending on the concentration of the sanitizing agent in the water. If the solenoid is energized during the active state, the valve 3 is opened and a desired amount of a sanitizing agent, for example, a solid oxidizer comprising potassium peroxymonopersulfate or a blend of sodium chloride and bromide, is dispensed from the sanitizing agent source 20a into the water. During the inactive state, no sanitizing agent is dispensed into the water.

From the foregoing description, those skilled in the art will readily appreciate that other types of sanitizing agent sources can also be used with the present sanitizing system 12. Accordingly, the following description of the specific components of the sanitizing system depicted in FIG. 1A is merely exemplary of one form the present invention can take.

Generator

Figure 2:
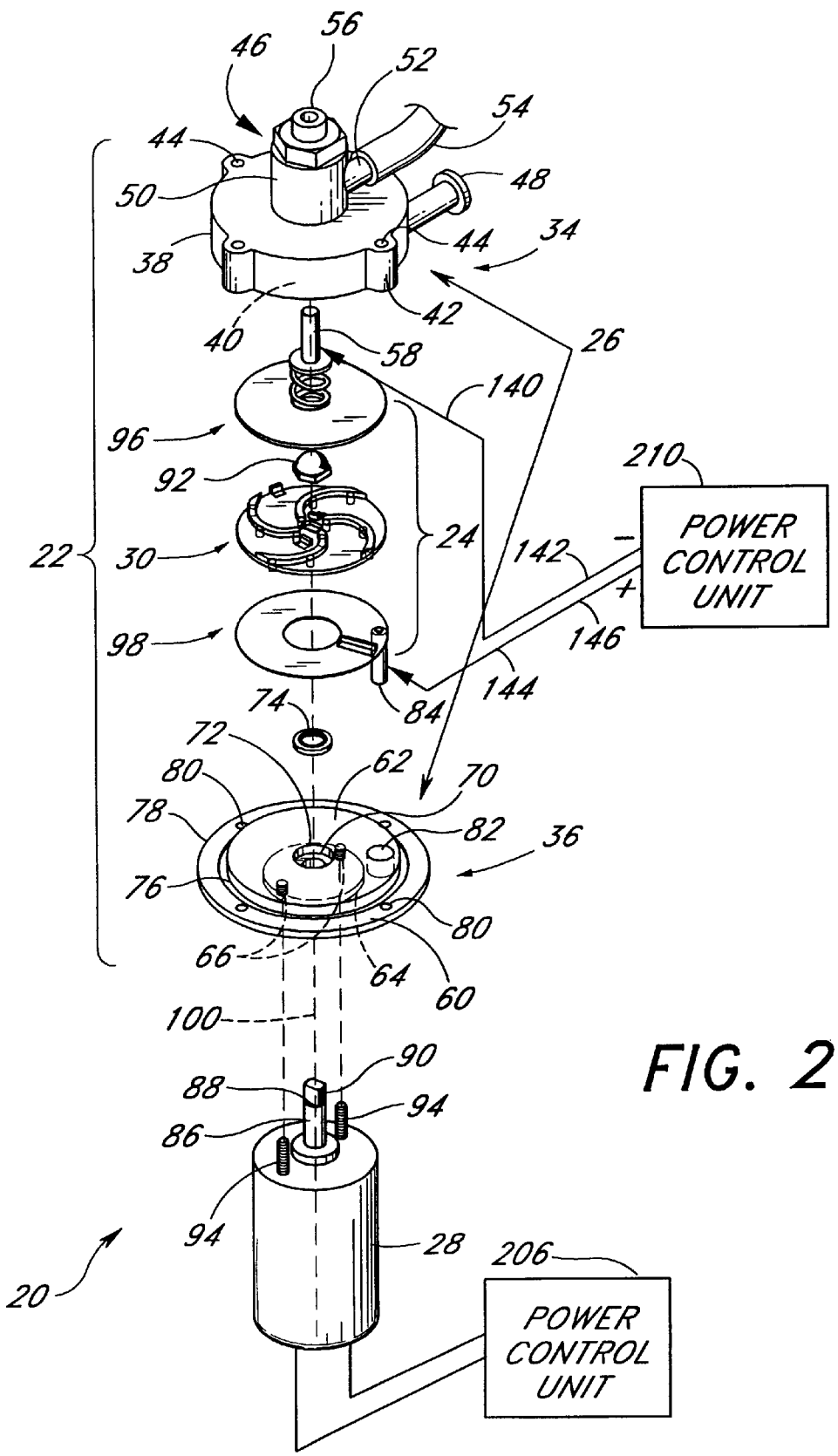
FIG. 2 is an exploded perspective view of a halogen generator configured in accordance with a preferred embodiment of the present invention.
Figure 3:
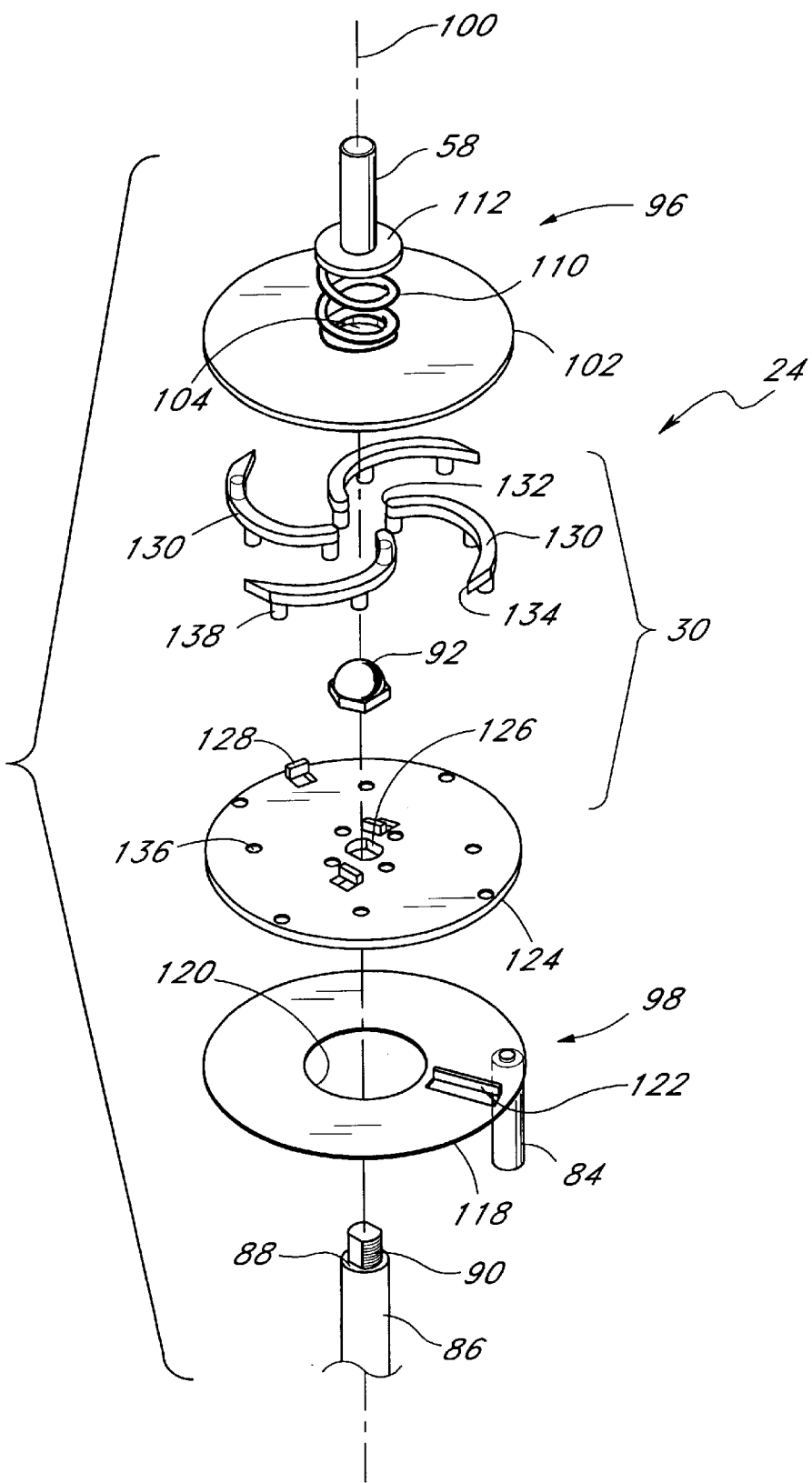
FIG. 3 is an exploded perspective view of an electrolytic cell of the halogen generator of FIG. 2 wherein a rotating bipolar electrode is positioned between a non-rotating anode and a non-rotating cathode.

With reference to FIGS. 2–3, the electrolytic cell 5 included in the generator has at least one cathode and at least one anode which form an electrode pairing which is connected to a voltage source, for example, included in the power supply unit 2. In another embodiment, the cell 5 may include two electrode pairings configured in a bipolar arrangement, as described below.

A preferred embodiment of the generator 20 is shown in FIG. 2. For the following description, this embodiment of the generator 20 is used to describe the invention. The generator 20 principally comprises a cell assembly 22 formed by an electrolytic cell 24 and a volute assembly 26 which houses the cell 24. A motor 28 drives an impeller 30 of the cell assembly 21 to create a flow of water through the cell 24, as described below.

The generator 20 also cooperates with the control unit 1 (FIG. 1). The control unit 1 controls the operation of the electrolytic cell 24 and the motor 28. The individual components of the generator 20 will now be described in detail with reference to FIGS. 2 and 3.

Volute Assembly The volute assembly 26 comprises a volute 34 and a volute plate 36 which together define an internal cavity in which the electrolytic cell 24 is housed. The volute 34 includes a generally cup-shaped housing 38 with a central cavity 40 having a cylindrical shape. The volute 34 also includes a plurality of lugs 42 which extend outwardly from the housing 38. A bolt hole 44 passes through each lug 42.

As understood from FIG. 2, the volute 34 includes an inlet port 46 and an outlet port 48. The inlet port 46 is configured to direct water flow into the central cavity 40 at the center of the volute assembly 26. The outlet port 48 is positioned on the peripheral edge of the housing 38, generally tangentially to the cylindrical central cavity 40 of the housing 28. This position of the outlet port 48 encourages water flow through the volute 34, as known in the art.

In the illustrated embodiment, the volute water inlet 46 includes a tubular segment 50 which extends axially from the center of the volute 34 and supports a bib 52. The bib 52 extends generally perpendicular to tubular segment 50. A water inlet conduit 54, which communicates with the water feature, is attached to the inlet port bib 52 to supply water to cell assembly 22.

The bib 52 communicates with the tubular segment 50 to form an inlet flow path though the inlet port 46. So configured, the flow path through the inlet port 46 turns 90° from the bib 52 into the tubular segment 50 to direct the flow of water into the cylindrically shaped central cavity 40 at the center of the cavity 40 and in a direction along the axis of the cavity 40.

As seen in FIG. 2, a plug 56 seals an outer end of the tubular segment 50. The plug 56 desirably has a tubular shape which allows a central terminal post 58 of the electrolytic cell 24 to extend through and out of the plug 56, as described below. The plug 56 desirably includes an O-ring (not shown) which sits against the terminal post 58 such that the plug 56 forms a seal between the tubular segment 50 and the cell terminal post 58 to prevent water flow through the outer end of the tubular segment 50. The plug 56 thus seals the fluid path through the inlet port 46.

The volute plate 36 of the volute assembly 26 includes a disc-shaped body 60 with raised central portions 62, 64 on either side of the body 60. The inner central portion 62 on the inner side of the volute plate 60 (i.e., the side which mates with the volute 24) desirably has a shape which is sized to snugly fit within the central cavity 40 of the volute 24. In the illustrated embodiment, the inner portion 62 has a cylindrical shape of a diameter which generally matches the diameter of the inner cavity. In this manner, the central portion 62 generally closes and seals the open end of the volute 34 so as to form the interior cavity of the cell assembly 22.

With reference to FIG. 2, the outer central portion 64 of the volute plate 36 has a size and shape to generally match that of an end of the motor 28. In the illustrated embodiment, the outer central portion 64 has a disc-like shape of a smaller diameter than the body 60 of the volute plate 36.

The body 60 and the outer central portion 64 of the volute plate 36 together define at least a pair of holes which extend into the volute plate 36 from its outer side. The holes are sized to receive threaded inserts 66 that are used to attach the motor 28 to the volute plate 36, as described below. The threaded inserts 66 desirably consist of stainless steel and are cemented to or integrally molded into the volute plate 36. In the illustrated embodiment, the holes lie on diametrically opposite sides of the center of the volute plate 36.

The volute plate 36 also defines a central bore 70 through its axial center with a first counterbore 72 circumscribing the bore 70 on the inner side of the plate 36. The counterbore 72 forms a seat for a conventional mechanical pump seal 74, as described below. A second counterbore (not shown) extends into the outer central portion 64 to form a relief.

The volute plate 36 also includes a circular groove 76 in the flange 78 which circumscribes the inner central portion 62. The groove 76 provides a seat for an O-ring (not shown). When assembled, the volute 34 and volute plate 36 compress the O-ring between an end of the volute 34 and the outer flange 78 to seal the union between these components.

A plurality of bolt holes 80 extend through the volute plate 36 about the peripheral edge of the outer flange 78. The bolt holes 80 desirably align with the corresponding bolt holes 44 formed in lugs 42 of the volute 34. A plurality of fasteners (e.g., bolts and nuts) pass through the aligned bolt holes 44, 80 and attach the volute plate 36 to the volute 34 when assembled.

The volute plate 36 also includes a hole 82 which extends though the inner central portion 62 and the disc body 60 at a location within the O-ring groove 76. The hole 82 is sized to receive a terminal post 84 of an electrode of the electrolytic cell 24, as described below.

The volute 34 and volute plate 36 desirably are formed of a nonconductive polymer, such as, for example acrylonitrile-butadiene-styrene (ABS). These components can be constructed in any of a wide variety of ways which will be well known to one skilled in the art. For example, these components can be integrally molded such as by injection molding.

Drive Motor FIG. 2 also illustrates the electric motor 28 which rotates the impeller 30 of the electrolytic cell assembly 22. The motor 28 may operate on either alternating or direct current (i.e., either an AC or DC motor) and desirably produces about 8 ounce-inches of torque or greater at a rotational speed of about 1,800–1,850 rpm. In the illustrated embodiment, the motor 28 is a 38 volt DC, 16 Watt motor, operated at 17–18 volt DC, with a diameter of about 1.6 inches (4.064 cm). It is, of course, understood that those skilled in the art can readily select a variety of conventional motors of various sizes and rotational speed and torque specifications in order to suit a specific application of the generator.

Direct current motors have the advantage of very high starting torque and low cost. Either brush or brushless designs can be used with the present halogen generator 20. Motor speed can be any speed resulting in the requisite outlet water pressure. One thousand to five thousand rpm is sufficient. Erosion of the catalytic coating due to high velocity can be held to a minimum by turning the impeller 30 at 1,500 to 3,000 rpm. At 1,500 rpm, the tip speed is roughly 487 cm per second, which is not excessive for electrode coatings. As discussed in detail below, the actual velocity the anode experiences is substantially less than that because the water is accelerated to a speed close to that of the impeller 30, with only the cathode being exposed to the high-velocity water.

The motor 28 includes a drive shaft 86 which extends into the internal cavity of the volute assembly 22 when assembled. In the illustrated embodiment, the drive shaft 86 comprises 316 stainless steel.

The end of the drive shaft 86 includes a shoulder 88 and a threaded stud 90. The shoulder 88 is configured such that the impeller 30 of the electrolytic cell assembly 22 sits on the shoulder 88 of the drive shaft 86 when assembled. As understood from FIG. 2, the threaded stud 90 desirably includes a pair of opposing flats which extend axially from the shaft end toward the motor 28. The resultant truncated circular cross-sectional shape of the stud 90 corresponds to a similar shape of a central aperture in the impeller 30 to key the impeller 30 to the shaft 28, as described below.

A nonconductive cap nut 92 secures the impeller 30 to the drive shaft 28. The cap nut 92 desirably is made of polyvinyl chloride (PVC) or like nonconductive, corrosion-resistant material. The nonconductive cap nut 92 insulates the shaft 28 from the upper conductive surface of the impeller 30. In this manner, the shaft 86 is cathodically protected from corrosion as it only contacts one side (i.e., the underside) of the impeller 30, as explained further below.

As understood from FIG. 2, the motor 28 also includes a pair of mounting holes which extend longitudinally through the body of the motor 28. The mounting holes are sized to receive mounting bolts 94 which extend through the motor body and engage the threaded inserts 66 of the volute plate 36. In this manner, the motor 28 is secured to the volute assembly 26.

Electrolytic Cell The electrolytic cell 24 includes at least one cathode 96 and at least one anode 98 which form an electrode pairing. In the illustrated embodiment, the cell 24 desirably includes two electrode pairings configured in a bipolar arrangement. That is, the cell 24 includes a cathode 96, an anode 98, and a bipolar electrode 30 (which functions as the impeller) interposed between the cathode 96 and the anode 98. The cathode 96 and the anode 98 polarize the corresponding sides of the electrode 30 such that one side of the electrode 30 function as an anode and the other side functions as a cathode to provide two cathode/anode pairings. As illustrated by the other embodiments of the electrolytic cell described below, however, any of a wide variety of cell configurations, which will be readily apparent to those skilled in the art, can be used with the present halogen generator 20.

FIG. 3 illustrates the electrolytic cell 24 in isolation. The bipolar cell 24 comprises the bipolar electrode 30 positioned between the cathode 96 and the anode 98. In the illustrated embodiment, the bipolar electrode 30, cathode 96, and anode 98 each have generally circular, disc-like shapes and are arranged in parallel along the common central axis 100. The electrode 30, the cathode 96, and the anode 98 desirably have a diameter of less than about 10 inches (25.4 cm), more preferably less than about 5 inches (12.7 cm), and most preferably equal to about 2.5 inches (6.35 cm). It is understood, however, that the electrode 30, cathode 96 and anode 98 can have any of a variety of other diameter sizes in order to suit a specific application and in order to give the anode 98 and cathode 96 a proper current density.

As described in detail below, both the cathode 96 and the anode 98 are mounted in a fixed rotational relationship within the cell assembly 22, while the bipolar electrode 30 rotates therebetween. In this manner, the bipolar electrode 30 functions as a pump impeller as described below.

The cathode 96 includes a circular plate 102 that defines a central bore 104 for the passage of water from the water inlet 46 of the volute 34 through the plate 102. The cathode plate 102 is made of an electrically conductive, corrosion resistant material. In the illustrated embodiment, the cathode plate 102 is made of 316L stainless steel or any other suitable metal, such as, for example copper or titanium. The cathode plate 102, however, also can be formed of a discontinuous material for enhancing scale removal from the cathode 96.

The thickness of the cathode plate 102 desirably ranges between about 0.020 and about 0.250 inches (0.0508 cm–0.635 cm), and preferably equals about 0.032 inches (0.0813 cm). A thinner cathode plate has more flexibility than a thicker plate, and flexure of the plate 102 tends to promote scale removal. In addition, in the case where the cathode plate 102 moves away from the volute 34, as described below, the surface of the cathode plate 102 which faces the volute 34 preferably is coated to prevent scale buildup thereon. The side of the cathode plate 102 which faces the bipolar electrode 30, however, desirably is uncoated and can be polished to an Ra surface finish of 8 to 16, which has been found to reduce scale formation on this inner surface of the cathode plate 102.

The cathode 96 desirably includes the terminal post 58 which is electrically connected to the cathode plate 102. The terminal post 58 has a diameter of approximately 0.125 inches (0.318 cm) or larger; however, it is understood that the post 58 can have any of a variety of diameter sizes in order to suit a specific application. As understood from FIG. 2, the terminal post 58 has a sufficient length so as to extend through the plug 56 to expose its outer end.

The cathode plate 102 desirably can move axially (i.e., in a direction parallel to the central axis 100) to enhance descaling of the cathode plate 102, as explained below. The cathode plate 102, however, preferably is biased into a desired position for normal operation. For this purpose, the cathode may comprise a biasing element or mechanism 110, such as a spring, which biases the cathode plate 102 into a first position for normal operation of the halogen generator 20 but allows the plate 102 to move to a second position to aid descaling of the cathode plate 102. In the illustrated embodiment, the spring has a spring constant of about 12 pounds/inch, where the normal flow rate through the volute assembly 26 is 1.1 gallons/min. (4.23 l/min.) and the flow rate during a cleaning cycle is 1.7 gallons/min. (6.54 l/min.). It is appreciated, however, that those skilled in the art will be able to calculate the desired spring constant for a specific application.

In the illustrated embodiment, the terminal post 58 is welded to a disc 112 which, in turn, is welded to the spring 110. The spring 110 provides an electrical connection between the terminal post 58 and the cathode plate 102, as well as allows relative movement of the cathode plate 102 toward the bipolar electrode 30, as discussed below. The spring 110 is welded to the cathode plate 102, about the bore 104. Heliarc welding is the preferred method of connecting the spring 102 to the plate 102 as it causes little deformation of the electrode plate 102. The disc 112 and spring 110 desirably have a diameter of a sufficient size to stably support the terminal post 58 above the plate 102, yet, as understood from FIG. 2, fit within the tubular segment 50 of the inlet port 46.

The anode 98 also comprises a circular disc or plate 118 which includes a central bore 120. The bore 120 receives the drive shaft 86 of the motor 28 when the cell assembly 24 is assembled, as described below.

The anode plate 118 is preferably made of titanium or any other suitable metal. The thickness of the anode plate 118 desirably ranges between about 0.020 and about 0.250 inches (0.0508 cm–0.635 cm), and preferably equals about 0.032 inches (0.0813 cm). The anode plate 118 is coated with precious metal oxides or other materials, such as, for example, a mixture of ruthenium oxide and titanium oxide, to promote the production of halogens through electrolysis.

The anode also includes the terminal post 84 which is electrically connected to the anode plate 118. The terminal post 84 is positioned on the plate 118 so as to extend through the volute plate hole 82 (FIG. 2) when assembled.

The post 84 has a diameter of about 0.125 inches (0.318 cm) or larger, and is welded to an outer edge of the anode plate 118. It is understood, however, that post 84 can have any of a variety of diameter sizes in order to suit a specific application. As understood from FIG. 2, the terminal post 84 has a sufficient length so as to extend through the hole 82 in the volute plate 36 to expose its outer end.

As seen in FIG. 3, a stationary vane or baffle 122 extends out of the plane of the anode plate 118. The baffle 122 can be either integrally formed with or separately formed from the anode plate 118 and is positioned to extend radially across the plate 118. In the illustrated embodiment, the baffle 122 comprises an integral tab which is bent out of the plane of the plate 118 to lie at an angle transverse to the plane of the plate 118.

FIG. 3 also illustrates the bipolar electrode impeller 30 of the electrolytic cell 24. The bipolar electrode 30 includes a circular disc 124 which preferably is made of titanium or any other suitable material. Various suitable coatings (e.g., precious metal oxides) for promoting the electrolytic production of halogens may be applied to the exterior surfaces of the bipolar electrode body 124. In the illustrated embodiment, the electrode disc 124 is coated with a mixture of ruthenium oxide and titanium oxide.

The electrode 30 is attached to the end of the motor drive shaft 86 so as to rotate between the anode and cathode plates 98, 96. In the illustrated embodiment, the disc 124 includes a central aperture 126 which has a complementary shape to the shape of the stud 90 on the end of the drive shaft 86. That is, the aperture 126 generally has a circular shape with a pair of opposing flats which gives the aperture 126 a generally flatten-elliptical shape.

The nonconductive nut 92 holds the electrode impeller disc 124 onto the end of the drive shaft 86, as described above.

As understood from FIG. 3, the electrode plate 124 desirably carries a plurality of small tabs 128 on the side of the plate 124 which faces the cathode 96. The tabs 128 are spaced apart from one another and are positioned at various locations about the disc 124, both in terms of angular and radial positions relative to the center of the plate 124. The tabs 128, however, desirably lie generally tangential to the rotation direction of the electrode plate 124. This orientation of the tabs 124 minimizes the frontal area of the tabs 128 as the tabs 128 rotate with the plate 124 through the water, thereby minimizing the drag the tabs 128 produce on the electrode plate 124.

The tabs 128 help reduce scale buildup on the cathode 96, especially in extremely hard water (e.g., hardness levels of 700 ppm and above). The tabs 128 contact large scale buildup on the cathode plate 102 and effectively chop the scale from the cathode plate 102. The sharp corners of the tabs 128 provide excellent abrading tools, and the tabs 128 are desirably left uncoated to enable oxide formation thereon to increase the abrasive quality of the tabs 128.

It should be understood, however, that the electrode impeller 30 can sufficiently descale the cathode 96 without the tabs 128 in water having normal to moderately high hardness levels (i.e., 300 ppm to 700 ppm). The addition of the tabs 128 thus improves the operation of the halogen generator 20 in extremely hard water.

Figure 3A:
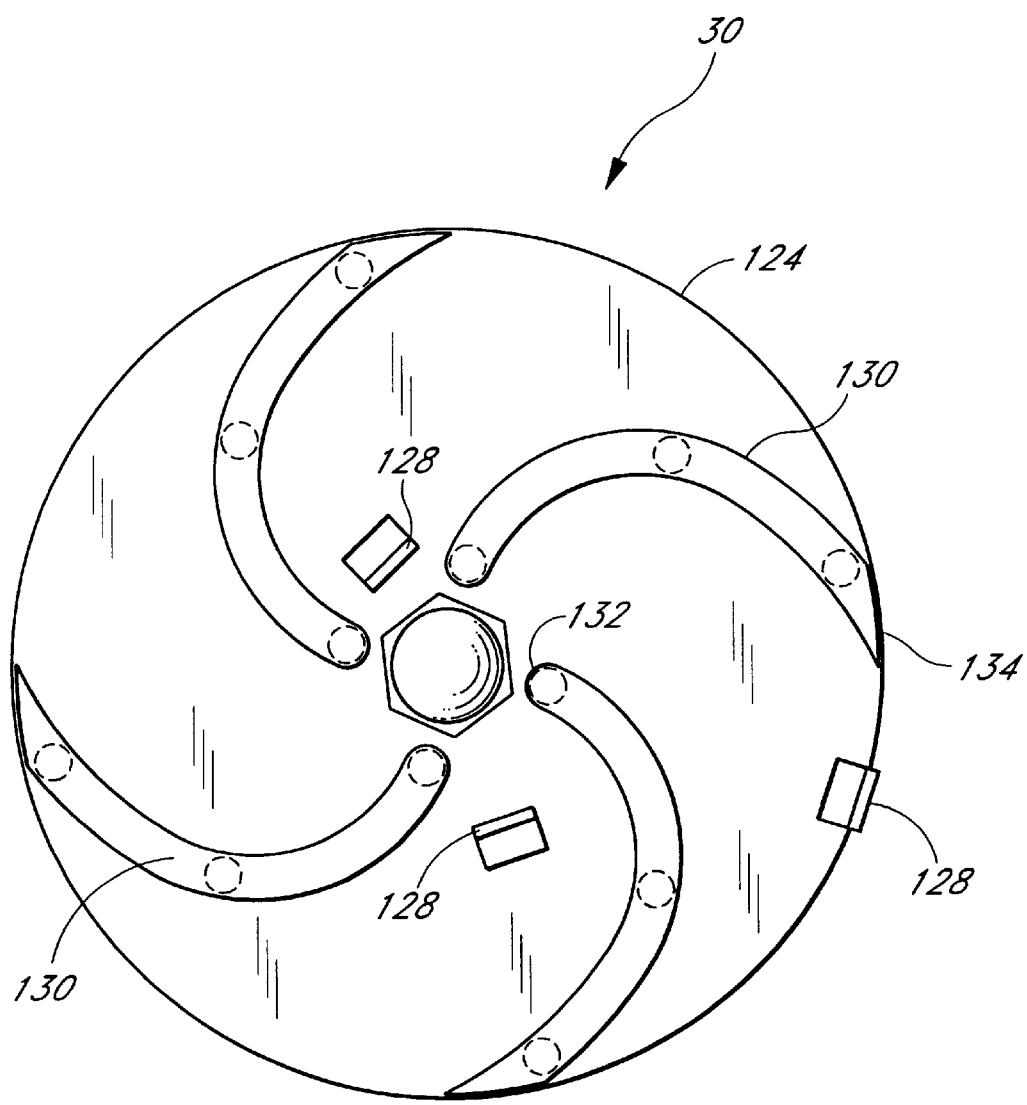
FIG. 3A is a top plan view of the bipolar electrode of FIG. 3.

As best seen in FIG. 3A, the tabs 128 are spaced about the center of the plate 124 at various distances from the plate center. In the illustrated embodiment, the plate 124 includes three tabs 128. The tabs 128 desirably are integrally formed with the plate 124 and are punched out to extend generally normal to the plane of the plate 124; however, it is contemplated that the tabs 128 could be separately formed and attached to the plate 124 in a known manner, such as, by spot welding, cementing, etc. The tabs 128 are positioned away from the center of the plate 124 at positions generally corresponding to a quarter of the radius, a half of the radius, and the full radius of the plate 124. Of course, other numbers and placements of the tabs 128 are possible.

As understood from FIGS. 3 and 3A, the electrode impeller 30 includes a plurality of curvilinear vanes 130 which are carried on and secured to the surface of the electrode plate 124 which faces the cathode 96. The vanes 130 are shaped and positioned so as to induce rotational movement of the water within the central cavity 40 of the volute 34. In the illustrated embodiment, the vanes 130 generally extend from the center of the electrode plate 124 and extend toward the periphery of the plate 124 in a spiral fashion. Each vane 130 includes a rounded inner end 132 and a tapering outer end 134 which generally conforms to the outer circular periphery of the bipolar electrode plate 124. The vanes 130 have a generally rectilinear cross-sections with flat surfaces facing the cathode 96. The vanes 130 desirably are about 0.100 inches thick with sharp edges formed between the sides and the flat surfaces.

The impeller vanes 130 desirably are made from plastic or a resilient material with PVC or other suitable polymer. The vanes 130 alternatively may be made of a metallic material, such as aluminum, and coated with a nonconductive, wear-resistant coating.

As seen in FIG. 3, the electrode plate 124 desirably includes a plurality of apertures 136 located on a side of the disc 124 that faces the cathode 96 to secure the vanes 130 to the plate 124. The apertures 136 are sized and positioned to receive pins 138 on the underside of a plurality curvilinear impeller vanes 130. In FIG. 3, the vanes 130 are shown exploded to better illustrate the pins 138 and the apertures 136 of the electrode plate 124.

The pins 138 may be press-fit into the apertures 136 and/or may be secured within the aperture 136 by partially deforming the ends of the pin 138 in a fashion similar to a rivet, either by melting or peening. The pins 138 also can be mechanically bonded, chemically bonded, or welded to a collar positioned on the opposite side of the electrode plate 124. It is also contemplated that the vanes 130 can be bonded to the electrode plate 124, in the alternative or in addition to attaching the pins 138 to the plate 124.

Generator Assembly With reference to FIG. 2, the terminal post 58 of the cathode 96 is inserted through the tubular segment 46 and the plug 56 to expose an outer end of the of the terminal post 58. A conventional retainer ring or like fastener (not shown) snaps onto the exposed end of the terminal post 58 to couple the cathode with the volute 34. The terminal post 58 may also be bonded to the plug 56 to secure the cathode 96 to the volute 34. A fluid seal is provided within the cathode plug 56 with, for example, an O-ring (not shown).

In this position, the cathode plate 102 desirable rest flush against the inner wall of the volute 34 with its central hole 104 coaxially positioned relative to the opening of the inlet port 46 (i.e., the tubular segment 50). The disc 112 and spring 110 of the cathode 96 are housed within the tubular segment 50 of the inlet port 46.

As understood from FIG. 2, a conductor 140 leading from a negative terminal 142 of the control unit 1 electrically connects to the outer end of the terminal post 58 to supply electricity to the cathode plate 102. The control unit 1 and its operation will be discussed below.

The motor 28 is attached to the volute plate 36, for example, by threading the elongated bolts 94, which pass through the motor body, into the threaded inserts 66 positioned on the outer side of the volute plate 36. So attached, the motor shaft 86 extends through the center hole 70 of the volute plate 36. A conventional mechanical pump seal 74, such as the type available commercially from Cyclam of France, is seated in the counterbore 72 on the inner side of the volute plate 36. The seal 74 creates a fluid-tight seal between the volute plate 36 and the motor shaft 86, while producing little friction or interference with the motor shaft 86 as it rotates.

The anode plate 118 is seated on the volute plate 36 with its terminal post 84 extending through the corresponding hole 82 in the volute plate 36. A conventional retainer ring or like fastener (not shown) snaps onto an exposed end of the terminal post 84 to secure the anode 98 to the volute plate 36. The volute plate hole 82 includes a fluid seal, such as an O-ring (not shown), to prevent fluid from exiting the cell through the hole 82. A conductor 144 leading from a positive terminal 146 of the control unit 1 electrically contacts the outer end of the terminal post 84 to supply electricity to the anode plate 118.

The bipolar electrode plate 124 is attached to the end of the shaft 86 by the nonconductive nut 92. Specifically, the plate 124 is inserted over a portion of the shaft 86 to rest on the shoulder 88 of the stud 90 of the shaft 86. The corresponding shapes of the aperture 126 in the electrode plate 124 and the shaft stud 90 key these components 86, 124 together to cause the electrode plate 124 to rotate with the motor shaft 86. The nonconductive nut 92 holds the electrode plate 124 on the end of the shaft 86. In this manner, the shaft 86 generally is electrically isolated from the other components in the electrical system. Fortunately, the motor armature usually is already insulated.

The volute plate 36 is placed on the end of the volute 34 with the electrode impeller 30 and anode 98 being inserted into the interior cavity of the volute 34. In this position, the anode plate 118, electrode plate 124 and cathode plate 102 lie generally parallel to one another. Bolts (not shown), passed through the corresponding bolt holes 44, 80 in the lugs 42 of the volute 34 and in the outer flange 78 of the volute plate 36, cooperate with nuts (not shown) to hold the volute 34 and volute plate 36 together.

When assembled, the electrode plate 124 desirably is equally distanced from the cathode plate 102 and the anode plate 118. The gap spacings between the electrode plate 124 and the anode plate 118 and between the electrode plate 124 and the cathode plate 102 desirably is sufficient to promote efficient electrolysis. That is, the gap spacings are set so as to maximize the efficiency of the electrolytic cell 24. In the illustrated embodiment, the gap spacings range between about 0.15 and about 0.75 inches, and preferably equal about 0.15 inches. The gap spacings, of course, can be selected in order to suit a specific application.

The spacing between the outer surface of the vanes 130 on the rotary electrode 30 and the cathode plate 102 importantly also are tightly controlled, especially for operation in hard water (i.e., water having a hardness of greater than 700 ppm). In the illustrated embodiment, the outer surfaces of the vanes 130 are spaced from the cathode plate 102 by a distance which preferably ranges between about 0.03 and about 0.1 inches (0.0762 cm–0.254 cm), more preferably ranges between about 0.03 and about 0.05 inches (0.0762 cm –0.127 cm), and most preferably equals about 0.03 inches (0.0762 cm). Although the vanes 130 are placed in close proximity to the cathode plate 102, the vanes 130 do not contact the cathode 96 when the electrode plate 124 rotates.

The close spacing between the vanes 130 and the cathode plate 102 prevents scale buildup on the cathode 96. As the bipolar electrode 30 rotates, the fluid velocity created at the surface of the cathode plate 102 by the vanes 130 substantially prevents scale from building up. Scale may temporarily form on the surface of the cathode plate 102, but the velocity of the water within the cell 24, and in particular, between the vanes 130 and the surface of the cathode plate 102, breaks the scale away from the plate surface 102. Water flow through the cell 24, which is produced by the vanes 130, carries the loose scale particles through the outlet port 48 of the volute assembly 26 to flush the scale particles from the cell assembly 22. In addition, the vanes 130 will mechanically knock-off any scale deposits in excess of the gap spacing between the vanes 130 and the cathode plate 102.

From surface friction, the flat bottom surface of the bipolar electrode 30 also creates some rotational velocity of the water between the bipolar electrode 30 and the anode 98. The baffle 122, however, substantially inhibits water from rotating close to the surface of the anode 98. This helps prevent erosion of the anode 98. The baffle 122 also inhibits the formation of substantial scale deposits on the underside of the bipolar electrode 30 which functions as a cathode. Like the vanes 130 on the opposite side of the rotary electrode 30, the baffle 122 lies close to the underside of the electrode 30. The close spacing between the baffle 122 and the electrode plate 124 causes a rapid change of water velocity between the rotating electrode 30 and the stationary baffle 122. In the illustrated embodiment, the outer surface of the baffle 122 is spaced from the rotary electrode 30 by a distance which preferably ranges between about 0.03 and about 0.1 inches (0.0762 cm–0.254 cm), more preferably ranges between about 0.03 and about 0.05 inches (0.0762 cm–0.127 cm), and most preferably equals about 0.03 inches (0.0762 cm). Although the baffle 122 is placed in close proximity to the electrode plate 124, the baffle 122 does not contact the electrode plate 124 as the plate rotates 124.

This small gap in which the water velocity changes from the rotational speed of the electrode 30 to zero velocity at the stationary baffle 122 greatly prevents the development of scale buildup on the underside of the electrode 30, much like the action between the vanes 130 and cathode plate 102. Scale may temporarily form on the cathodic surface of the electrode 30, but the velocity of the water within the cell 24, and in particular, between the baffle 122 and the cathodic surface of the electrode 30, breaks the scale away to be flushed out of the cell assembly 22. In addition, scale buildup on the cathodic surface of the electrode 30 in excess of the gap spacing between the baffle 122 and the electrode plate 124 is knocked off by mechanical contact with the baffle 122.

Control Unit

Figure 4:
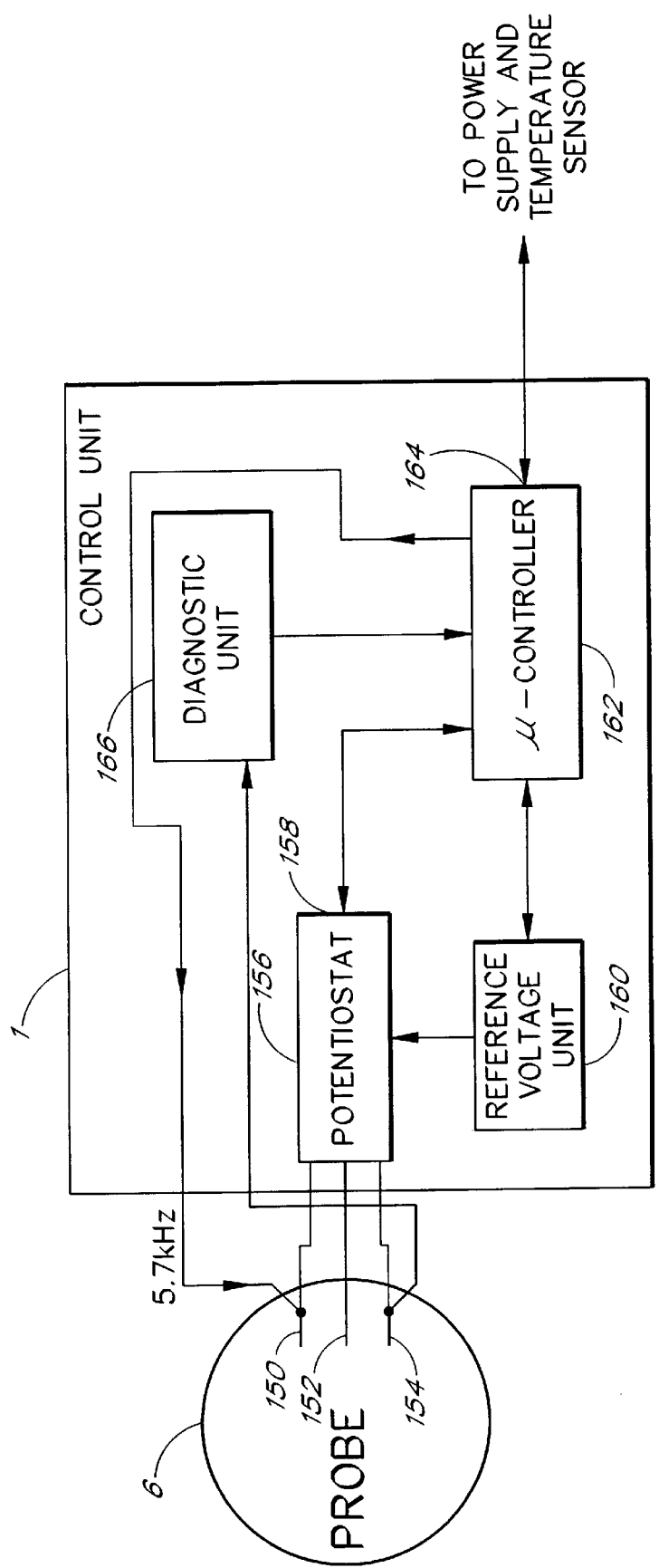
FIG. 4 is a simplified illustration of a control unit connected to a sensor probe.

FIG. 4 shows a simplified illustration of the control unit 1 to indicate some main components, their principal interconnections and their positions with respect to the sensor probe 6. A more detailed illustration of the control unit 1 according to the present invention is shown in FIG. 5.

The control unit 1 operates the generator 20 via the power supply 2 according to characteristics obtained from the sensing system, i.e., the sensor probe 6, the optional temperature sensor 13, and the optional pH sensor integrated with the sensor probe 6. For this purpose, the control unit 1 houses a potentiostat 156 of the amperometric sensor for amperometric measurement. The potentiostat 156 is connected to the sensor probe 6. More particularly, the potentiostat 156 is connected to three sensor probe electrodes, namely a working electrode 150, a counter (or auxiliary) electrode 152 and a reference electrode 154. The control unit 1 further comprises a reference voltage unit 160, which provides several reference voltages to the potentiostat 156, and a microcontroller 162 which is, for example, a 8-bit CMOS microcontroller PIC16C72 available from Microchip Technology Inc.

As described below in detail, the microcontroller 162 is coupled to the potentiostat 156, to the reference voltage unit 160, via a capacitor and a solenoid operated switch (not shown) to the working electrode 150 of the sensor probe 6, and to a diagnostic system 166 which is also housed in the control unit 1. The diagnostic system 166 is additionally connected, via a solenoid operated switch (not shown) to the reference electrode 154 of the sensor probe 6. The microcontroller 162 has several other inputs and outputs which are connected to the power supply unit 2 and to the optional temperature sensor 13, as shown in FIG. 1. These inputs and outputs are generally indicated as port 164 in FIG. 4.

Figures 5, 5A:
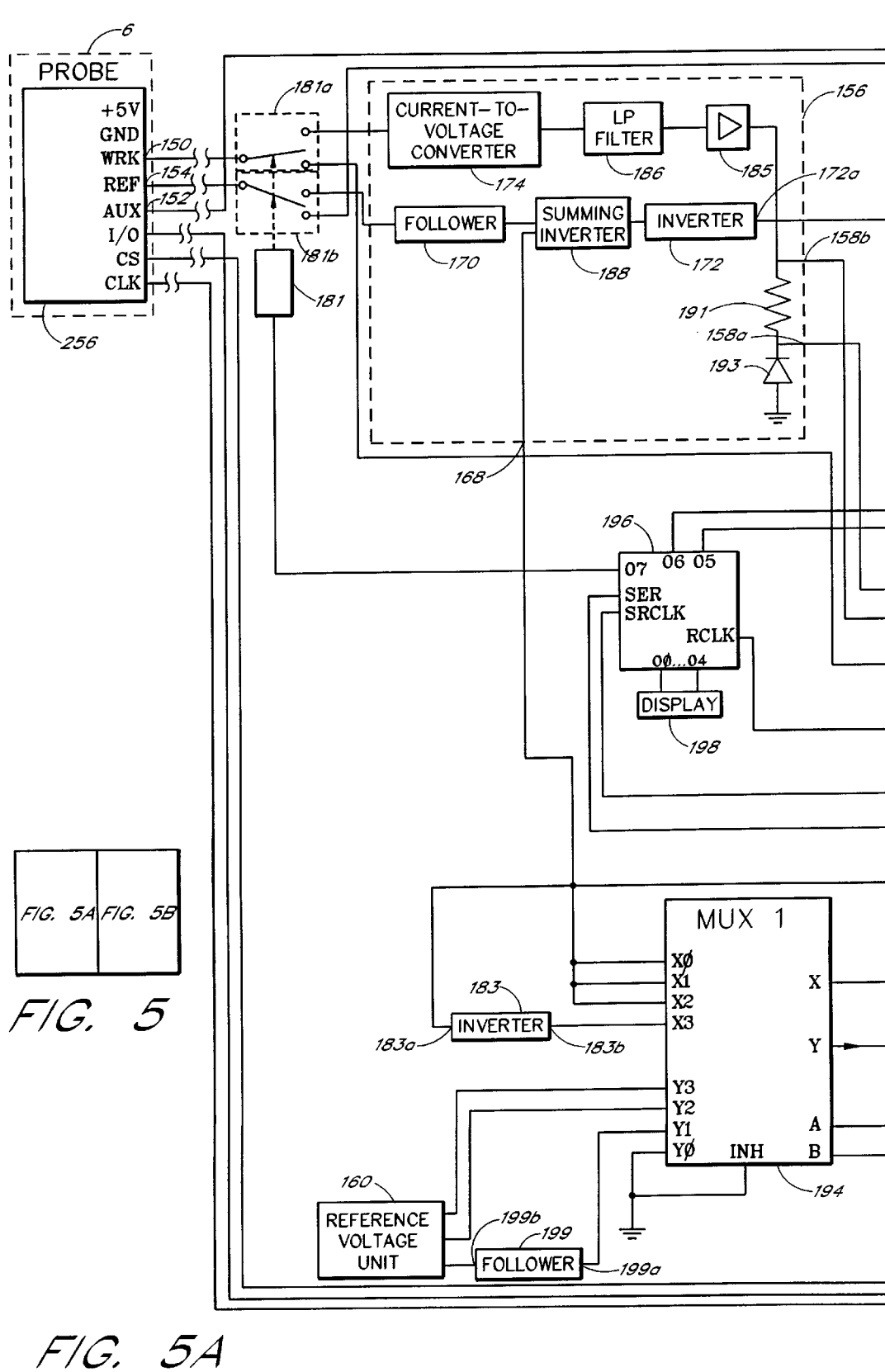
FIG. 5, comprising FIGS. 5A an 5B, is a detailed illustration of a control unit shown in FIG. 4.
Figure 5B:
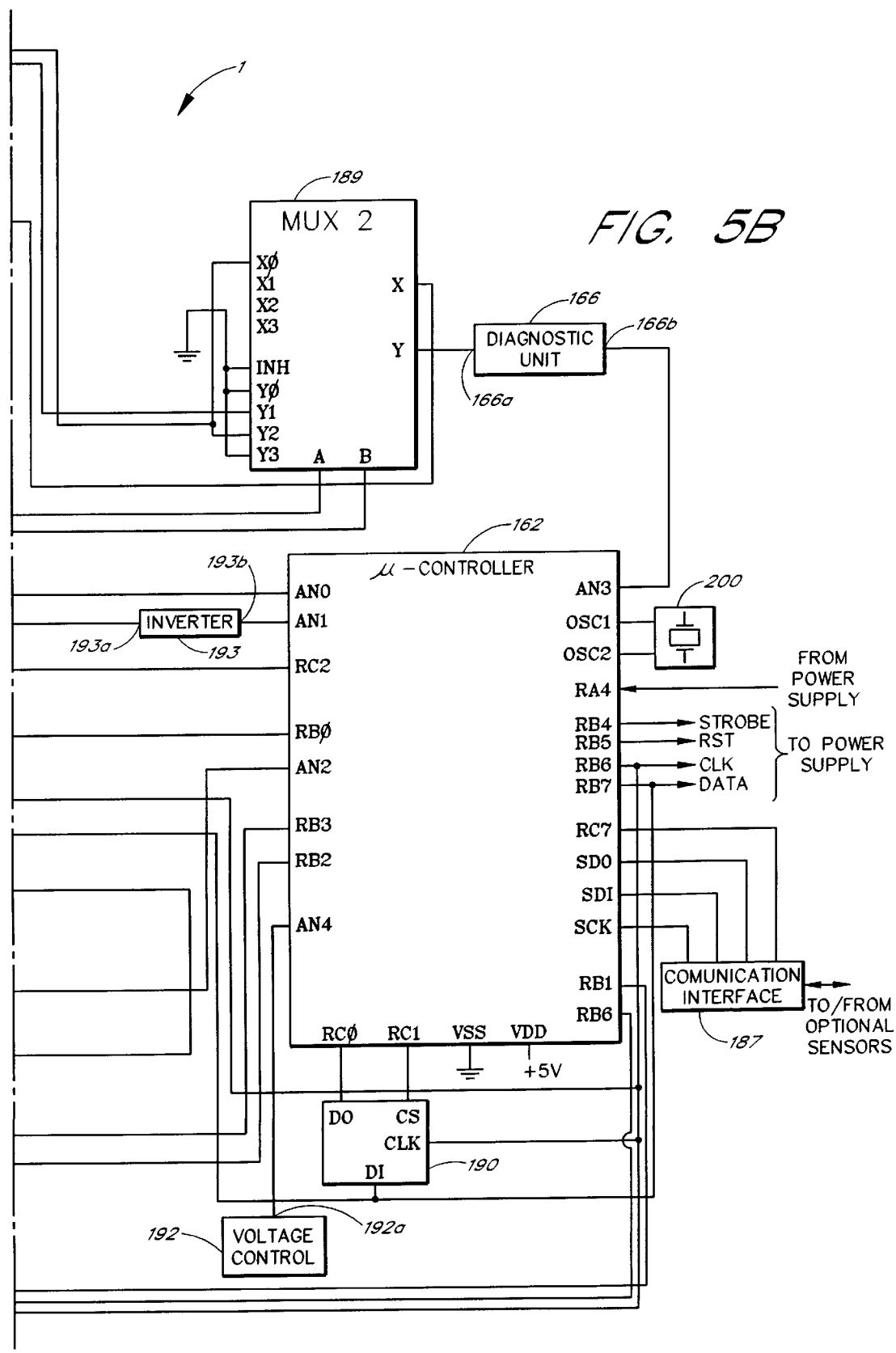

A more detailed illustration of the control unit 1 is shown in FIG. 5 in which the sensor probe 6 is generally indicated by means of a connector having connecting ports +5 V, GND, WRK, REF, AUX, I/O, CS and CLK, which will be described below in connection with FIG. 10. The control unit 1 comprises a first multiplexer 194 that is used as an interface between the microcontroller 162, the potentiostat 156 and the reference voltage unit 160. A second multiplexer 189 interfaces the potentiostat 156 and the diagnostic system 166.

The multiplexers 194, 189 desirably are dual 4-channel analog multiplexers MM74HC4052 available from National Semiconductor. Each multiplexer 194, 189 has two sections X, Y. The X section includes a first set of inputs X0–X3 and a respective first output X. The Y section includes a second set of inputs Y0–Y3 and a respective second output Y. The multiplexer 194 also includes several control outputs A, B and INH which control selection of one of the X0–X3 inputs to the X output and also controls the selection of one of the Y0–Y3 inputs to the Y output. Furthermore, the multiplexers 194, 189 can be operated bidirectionally, i.e., a signal fed to an "output" X, Y is output at an "input" X0–X3, Y0–Y3.

Each multiplexer 194, 189 connects together the outputs of four switches in two sections, thus achieving a pair of 4-channel multiplexers. A binary code placed on the control inputs A and B determines which switch in each four channel section is "on", connecting one of the four inputs in each section to its common output X or Y. The inhibit control input INH when high disables all switches to their off state. In the illustrated embodiment, the control input INH is permanently grounded thereby enabling the switches to the "on" state. Further details can be obtained from the corresponding data sheet.

The potentiostat 156 comprises a plurality of operational amplifier devices. In FIG. 5, four operational amplifier devices illustrated as a follower 170, an inverter 172, a current-to-voltage converter 174 and a summing inverter 188, as well as their electrical interconnections are indicated. Details of the operational amplifier devices 170, 172, 174, 188 will be described below in connection with FIG. 6. The potentiostat 156 can be accomplished with a lesser number of operational amplifier devices, for example, two operational amplifier devices, as also described below.

In the illustrated embodiment (FIG. 5), the potentiostat 156 also comprises a low pass filter 186 and an amplifier 185. The low pass filter 186 is positioned in series between the current-to-voltage converter 174 and the amplifier 185. The low pass filter 186 serves to block frequencies above a cut-off frequency, i.e., an AC component present in the output signal of the amplifier device 174 is blocked.

The low pass filter 186 included in the potentiostat 156 is preferably an active filter of second order. Such an active filter comprises two serial resistors, two capacitors and an operational amplifier. The two resistors have values in the range of about 1 Mega Ohms and the two capacitors have values in the range of about 0.1 Micro Farad. The two resistors are connected between the output of the operational amplifier device 174 and the non-inverting input of the operational amplifier of the filter 186. One terminal of the first capacitor is connected to the input of the operational amplifier and its other terminal is grounded. One terminal of the second capacitor is connected between the two resistors and its other terminal is connected the inverting input of the operational amplifier. The inverting input is also connected to the operational amplifier output. Of course, other types of low pass filters can also be used.

An output of the amplifier 185 is connected to an output 158b of the potentiostat 156 and to a first port of a resistor 191. A second port of the resistor 191 is connected to an output 158a of the potentiostat 156 and to a first port of a diode 193, its second port being grounded.

The microcontroller 162 desirably includes a RAM, three timer/counters, a 5-channel high-speed 8-bit A/D converter (not shown) associated with analog ports AN0–AN4, and a variety of input/output ports RA, RB, RC, SDI, SDO. Further details are provided in the data book PIC16C7X DATA SHEET available from Microchip Technology Inc. The microcontroller 162 is grounded (port VSS) and connected to a +5 volts power supply (port VDD).

The control unit 1 further comprises a shift register 196 which is a 8-bit shift register with output latches, such as that available from National Semiconductor, as part number MM74HC595. The device contains an 8-bit serial-in, parallel-out shift register that feeds an 8-bit D-type storage register. Further details can be obtained from the corresponding data sheet. The shift register 196 has eight outputs O0–O7, and its inputs include a serial data input SER and two clock inputs SRCLK, RCLK. The outputs 05, 06 of the shift register 196 are connected to the second multiplexer 189 (A, B) and the outputs O0–O4 are connected to a display 198. Because the microcontroller 162 has a limited number of input/output ports, the shift register 196 is used to provide additional output ports for the microcontroller 162.

The display 198 desirably comprises five light emitting diodes (LEDs), each connected to an output O0–O4 of the shift register 196 and to a serial resistor (not shown) connected to a +5 volts power supply. It will be understood by those skilled in the art that the display 198 can also take a variety of other forms, such as, for example, a liquid crystal display (LCD) device. The display 198 indicates continuously or only on request if the concentration of bromine is within or out of the preset range, if the motor and/or the cell are currently active, or an error code to facilitate maintenance of the system.

A memory device 190 comprised in the control unit 1 desirably is an electrically erasable programmable read-only memory (EEPROM), for example, a Microchip 93LC46 EEPROM, and stores a variety of information, including, but not limited to parameters used for reset operations, the duration of cell usage, the number of cell on-cycles and other system information, as described below. In the illustrated embodiment, the control unit 1 includes the memory device 190; however, those skilled in the art will appreciate that the system information stored in the memory device 190 can be also stored at other locations such as, for example, in a memory positioned within the probe 6 as described below in connection with FIGS. 9A, 10. In this case, the memory device 190 can be omitted.

The control unit 1 further comprises a crystal oscillator 200 which is connected to the microcontroller 162 and serves as a clock reference for the microcontroller 162.

The above-mentioned components of the control unit 1 are interconnected to each other, as described below. The inputs Y2, Y3 of the first multiplexer 194 are connected to outputs of the reference voltage unit 160, and the input Y0 is grounded. The input Y1 is connected to an output 199a of a voltage follower 199 which has an input 199b connected to an output of the reference voltage unit 160. The output Y is connected to the inputs X0, X1, X2 of this multiplexer 194, and to an input 183a of an inverter 183. An output 183b of the inverter 183 is connected to the input X3 of the multiplexer 194. The output Y is further connected to an input 168 of the potentiostat 156, which is connected to the summing inverter 188. The output X of the multiplexer 194 is connected to an input AN2 of the microcontroller 162. The multiplexer's control input A is connected to a microcontroller output RB3, and the control input B is connected to a microcontroller output RB2.

With reference to the second multiplexer 189, the input X0 is connected to the input Y2 and to the counter electrode 152. The inputs X1, X2, X3 are not used in the illustrated embodiment. Because the second multiplexer 189 can be operated bidirectionally, the output X functions as an input for the second multiplexer 189, and the inputs X0–X3 function as outputs. As illustrated, the "input" X is connected to an output 172a of the inverter 172 which is included in the potentiostat 156. The inputs Y0, Y3 are grounded, together with the control input INH. The input Y1 is connected to a switch 181b for connecting either the input Y1 or the follower 170 to the reference electrode 154. The switch 181b as well as a second switch 181a are controlled by a solenoid 181. By activating the solenoid 181, the microcontroller 162 can switch the control unit 1 from a measurement mode to a conductivity mode, as described below. The switch 181a connects either the current-to-voltage converter 174 or an output RC2 of the microcontroller 162 to the working electrode 150. The output Y is connected to an input 166a of the diagnostic system 166 having an output 166b which is connected to an input AN3 of the microcontroller 162. The control input A is connected to an output O6 of the shift register 196, and the control input B is connected to an output O5 of the shift register 196. An output O7 of the shift register 196 is connected to the solenoid 181 in order to forward control signals from the microcontroller 162. The remaining outputs O0 ... O4 of the shift register 196 are connected to the display 198. A serial data input SER of the shift register 196 is connected to a microcontroller output RB7 which outputs a data signal DATA. A clock input SRCLK is connected to a microcontroller output RB6 which outputs a clock signal CLK; and a clock input RCLK is connected to a microcontroller output RB0.

The crystal oscillator 200 is connected to microcontroller inputs OSC1 and OSC2 and oscillates at a frequency of 3.579 MHz. The microcontroller 162 uses this frequency to generate a low-frequency signal (e.g., 5.7 kHz) which is output at the output RC2 and fed to a port of the switch 181a which connects the working electrode 150 either to the output RC2 or to the current-to-voltage converter 174.

An input AN4 of the microcontroller 162 is connected to an output 192a of a voltage control unit 192. The output of the voltage control unit 192 is approximately +4.5 volts if the power supply provides −5 volts, and goes down to zero when the power supply for the electrical circuits does not provide the required −5 volts.

The EEPROM 190 has a clock input CLK which is connected to the microcontroller output RB6, and has a data input DI which is connected to the microcontroller output RB7. Furthermore, the EEPROM 190 has an output DO which is connected to a microcontroller input RC0, and has an input CS which is connected to a microcontroller output RC1.

A microcontroller input RA4 is adapted to receive signals originating from the power supply unit 2. The microcontroller 162 also generates a reset signal RST on a port RB5, and a control signal STROBE on a port RB4, both of which are provided to the power supply 2 (see FIG. 7).

Further, the microcontroller 162 has input/output ports RC7, SDO, SDI, SCK which are connected to a communication interface 187. Additional sensors, such as for temperature, pH or spa activity may be connected to the communication interface 187.

The output 158a of the potentiostat 156 is connected to an input AN0 of the microcontroller 162, and the output 158b of the potentiostat 156 is connected to an input 193a of an inverter 193. An output 193b of the inverter 193 is connected to an input AN1 of the microcontroller 162.

The microcontroller 162 has an input/output port RC6 that is connected to the input/output port I/O of the probe 6, and an output RB1 that is connected to the port CS of the probe 6.

Figure 6:
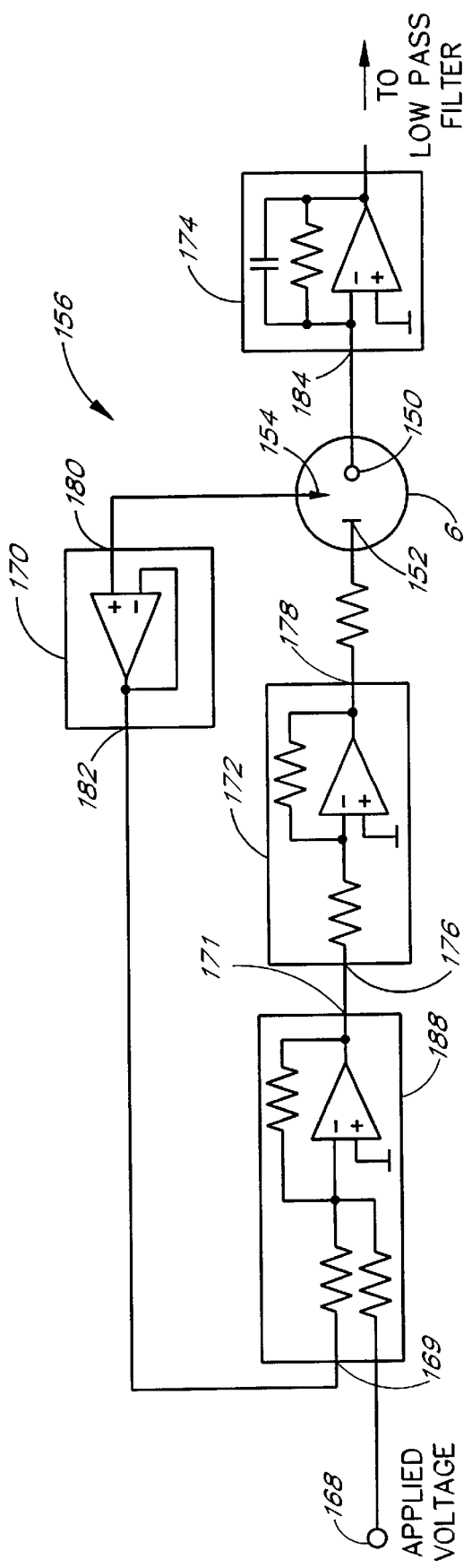
FIG. 6 is a principle illustration of a potentiostat housed within a control unit and connected to a sensor probe.

FIG. 6 illustrates the details of the potentiostat 156. In the illustrated embodiment, the potentiostat 156 comprises the operational amplifier devices 170, 172, 174, 188. (The low pass filter 186 and the amplifier 185 (FIG. 5) are not shown.) Each operational amplifier device 170, 172, 174, 188 comprises an operational amplifier and some additional electrical components such as resistors and/or capacitors. Those skilled in the art will understand that operational amplifiers can operate in various operational modes depending on the electrical components and their connection to the operational amplifier. In the simplified block diagram of FIG. 6, each operational amplifier is associated with one or more resistors and indicated as a block to assist the understanding. Those skilled in the art usually refer to such a block simply by means of its function, for example, inverter or follower.

The operational amplifier of the first operational amplifier device 170 is in an operational mode known as follower and has a non-inverting input 180 connected to the reference electrode 154 of the probe 6 and has an output 182. The inverting input of the follower is connected to its output. As seen in FIG. 6, the operational amplifier of the second operational amplifier device 172 is in an operational mode known as inverter and has an inverting input 176 and an output 178 which is connected to the counter electrode 152. The non-inverting input of the inverter is grounded. The inverting input 176 is connected to an output 171 of a third operational amplifier device 188, its operational amplifier is in an operational mode known as summing inverter. The inverting input 169 of the operational amplifier is connected to the output 182 and to the input 168. The third operational amplifier device 188, i.e., the summing inverter, outputs a voltage which is the negative sum of input voltages received from the output 182 of the follower and the input 168 of the potentiostat 156 from the reference voltage unit 160. The inverter of the second operational amplifier device 172 with gain of −1 receives this negative sum and outputs a positive voltage that is fed to the counter electrode 152. This voltage causes a current flow between the working electrode 150 and the counter electrode 152. In this manner, the potentiostat 156 is used to keep the potential between the working and reference electrodes 150, 154 at a desired constant value. For sensing bromine, this value preferably is in the range between −0.5 and +0.4 volts. More preferably within the range −0.1 and +0.3 volts, and most preferably within the range of +0.2 and +0.3 volts. In an exemplary embodiment, the potential between the working and reference electrodes 150, 154 is maintained at +0.3 volts. The desired potential to be maintained between the working and reference electrodes 150, 154 for sensing other sanitizing agents (e.g., other chemical species) can be readily determined empirically using well-known analytical technologies associated with conventional amperometry.

The operational amplifier of the fourth operational amplifier device 174 is operated in an operational mode know as current-to-voltage converter. Therefore, the operational amplifier device 174 is subsequently referred to as I/V converter (current-to-voltage converter). It has an inverting input 184 connected to the working electrode 150 and has an output which is the output 158 of the potentiostat 156. The non-inverting input of the I/V converter 174 is also essentially grounded and serves to maintain the working electrode 150 at ground potential. That is, although not actually grounded, the I/V converter 174 maintains the working electrode 150 at a virtual ground for all practical purposes. The I/V converter 174 provides at the output 158 a voltage proportional to the current flow between the working electrode 150 and the counter electrode 152.

The output 182 of the follower 170 and the input 169 of the adder 188 are connected to the input 168 of the potentiostat 156 to which a desired voltage is applied in order to sense a specific sanitizing agent. For instance, a voltage of about +300 millivolts (mV) is applied to sense bromine. With this voltage applied at the input 168, the potentiostat 156 generally stabilizes the voltage between the reference electrode 154 and the working electrode 150 generally equal to +0.3 volts for sensing bromine.

The feedback loop, which includes the reference electrode 154 and the follower 170, causes the potentiostat 156 to compensate for variations in the impedance across the working and counter electrodes 150, 152 which are due to factors other than the fluctuating concentration levels of the particular sanitizing agent being sensed. The high impedance created by the follower 170 within the feedback loop though insures that practically no current flows through the feedback loop. Then the current flow between the working and counter electrodes 150, 152, and thus the impedance through the electrolyte will be a function of the targeted sanitizing agent concentration in the spa water.

As mentioned above, the potentiostat 156 can include only two operational amplifiers devices. In such a circuit, an input of the first operational amplifier device is connected to the working electrode 150 and operates as current-to-voltage converter, as described above. An output of the second operational amplifier device is connected to the counter electrode 152, and the inverting input of the second operational amplifier device is connected to the reference electrode 154. The non-inverting input of the second operational amplifier device receives the applied voltage.

Power Supply Unit

Figure 7:
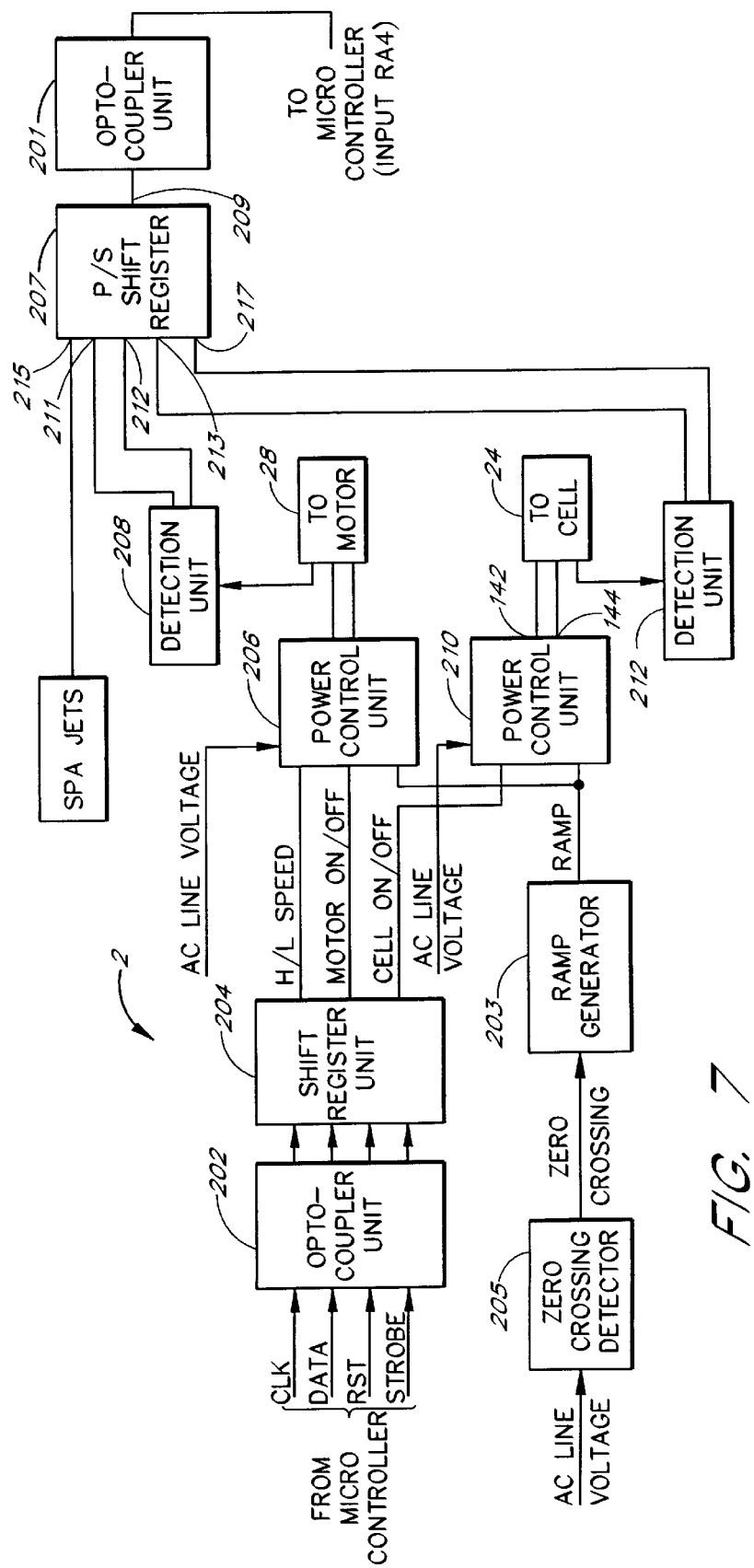
FIG. 7 is an illustration of a power supply unit shown in FIG. 1.

FIG. 7 shows an illustration of the power supply unit 2 shown in FIG. 1. The power supply unit 2 desirably comprises an opto-coupler unit 202 and a shift register unit 204. The opto-coupler unit 202 has several inputs for electrical control signals such as the CLK, DATA, RST and STROBE received from the microcontroller 162 (see FIG. 5), and a like number of outputs which are connected to inputs of the shift register unit 204.

The shift register unit 204 includes an 8-bit shift register with output latches such as a MM74HC595 available from National Semiconductor (see above), and a Schmitt Trigger IC, for example, an MM74HC14 available from National Semiconductor having six inverting Schmitt Trigger. The Schmitt Trigger IC shapes the electrical control signals CLK, DATA, RST and STROBE output from the opto-coupler unit 202 before they are input to the shift register. Data bits are clocked into the shift register according to the control signal CLK, and output from the shift register according to the control signal STROBE. Signals output from the shift register control the generator 20 shown in FIG. 1. These signals include MOTOR ON/OFF, H/L SPEED and CELL ON/OFF signals.

Although the meanings of the signals MOTOR ON/OFF, H/L SPEED and CELL ON/OFF are believed to be self-explanatory, a short description is given:

MOTOR ON/OFF controls the motor 28 between active and inactive states;

H/L SPEED controls the rotational speed (high or low) of the motor 28 and therefore controls the water flow rate through the cell 24; and CELL ON/OFF controls the cell 24 between energized and deenergized states.

The power supply unit 2 additionally comprises first and second power control units 206, 210. The first power control unit 206 is connected to the shift register unit 204 and receives the signals MOTOR ON/OFF and H/L SPEED and additionally receives a signal RAMP. The first power control unit 206 desirably includes an AC to DC converter to convert AC line current to direct current. Outputs of the first power control unit 206 are connected to the motor 28 (shown in FIGS. 2 and 7). The second power control unit 210 is also connected to the shift register unit 204 and receives the signal CELL ON/OFF. Additionally it receives the signal RAMP. The second power control unit 210 also includes an AC to DC converter to convert the AC line current to direct current. Positive and negative outputs 142, 144 of the second power control unit 210 are connected to the cell 24 (shown in FIGS. 2 and 7). The first power control unit 206 interfaces a line power source (e.g., 120 volts) with the motor 28, and inter alia, transforms the line voltage to one or more lower voltages and controls the voltages or currents applied to the motor 28. Likewise, the second power control unit 210 connects a line power source (e.g., 120 volts) to the cell 24, inter alia, transforms the line voltage to one or more lower voltages and controls the voltages or currents applied to the cell 24.

The power control units 206, 210 receive the signal RAMP which represents the charging voltage across a capacitor in a ramp generator 203. The charging is triggered at each zero crossing of the power line voltage occurring at a frequency of 100 Hz/120 Hz (i.e., twice the power line frequency). The zero crossings also serve as a time base for a conventional watchdog timer (not shown) in the automatic sanitizing system 12. A conventional zero crossing detector 205 can be implemented, for example, using a diode bridge and a current limiting resistor.

The power supply unit 2 also includes first and second detector units 208, 212. The first detection unit 208 is coupled to the motor 28 and to the microcontroller 162. In the illustrated embodiment, the detection unit 208 comprises a voltage amplifier to amplify a motor signal received from the motor 28, and two comparators to compare the amplified motor signal with different preset threshold values. One comparator detects a high motor current and the other detects if no motor current is present. The amplifiers desirably are included in integrated circuits, such as that available from National Semiconductor, as part number LM324A. The detection unit 208 monitors the operation of the motor 28, and detects if the current is too high or too low (e.g., zero). The unit 208 in response to these detections generates a signal which indicates the operational condition of the motor (e.g., "motor current high" or "no motor current") and provides the signal to the microcontroller 162 for further processing.

Similarly, the detection unit 212 includes a voltage amplifier and two comparators monitors. The voltage amplifier amplifies a cell signal received from the cell 24, and the two comparators compare the amplified cell signal with different preset threshold values. One comparator detects a high cell current and the other detects if a low cell current is present. The detection unit 212 thus monitors the operation of the cell 24, and detects if the current is too high or too low (e.g., zero). The unit 212 in response to these detections generates a signal which indicates the operational condition of the cell (e.g., "cell current low" or "no cell current") and provides the signal to the microcontroller 162 for further processing.

The signals from the detection units 208, 212 desirably are not directly input to the microcontroller 162. As seen in FIG. 7, a shift register 207 and an opto-coupler unit 201 act as an interface between the detection units 208, 212 and the microcontroller 162. In the illustrated embodiment, the shift register 207 which receives its clock signal from the microcontroller 162 is a 8-bit serial shift register such as a 74HC165 available from National Semiconductor. The shift register 207 shifts parallel input data to a serial (inverting) output 209 which is connected to the opto-coupler unit 201. An output of the opto-coupler unit 201 is connected to the input RA4 of the microcontroller 162. In the illustrated embodiment, the opto-coupler units 201, 201 form part of and are housed within the power control unit 2; however, the opto-coupler units 201, 202 can also be positioned outside the power control unit 2, i.e., between the power supply unit 2 and the microcontroller 162.

The opto-coupler unit 201 converts an electrical signal received from the shift register 207 to an optical signal, for example, by means of a photodiode, and then back to an electrical signal, for example, by means of a phototransistor. In the same manner, the opto-coupler unit 202 converts received electrical control signals first to optical signals and then back to electrical signals. By means of the opto-coupler units 202, 201 the control unit 1 and the power supply unit 2 are electrically isolated from each other so that no common ground exists between them. Further details regarding such an isolation will be explained in greater detail in connection with FIG. 15.

Two outputs from each detection unit 208, 212 are connected to shift register inputs 211, 212, 213, 217. These inputs 211, 212, 213, 217 receive the signals generated by the detection units 208, 212, and the shift register 207 serially outputs the signals to the microcontroller 162.

Another shift register input 215 communicates with the spa jet pump (either a booster pump or a high speed setting on the main spa pump) so that it receives a signal when the spa jet pump are activated. This signal is also forwarded to the microcontroller 162 which detects the spa usage.

Sensor Probe

FIGS. 8A through 10 illustrate a preferred embodiment of the sensor probe 6 used in the automatic sanitizing system 12. An exploded view of the sensor probe 6 is shown in FIG. 8A. The following description uses the terms "front" and "rear" in describing various components of the probe 6. These terms are used in reference to the water flow through water circulation line 9, such that "front" implies proximate to the water flow and "rear" implies distal of the water flow.

A tube 248, which has a front end 246 and a rear end 250, desirably forms a body of the sensor probe 6. The front end 246 fits into a receptacle of an adapter 224. The adaptor has a reduced-diameter, threaded front nipple 222 that threads into a threaded receptacle 220 of a T-fitting 218. The T-fitting 218 also includes two side ends 214, 216 adapted to be integrated into the water circulation line 9 shown in FIG. 1. In the illustrated embodiment, the ends 214, 216 include barbed nipples which insert into flexible hoses that desirably form a portion of the circulation line 9.

A cap 258 is attached to the rear end 250 of the tube 248, and a cup- or cylinder-shaped rubber boot 260 covers an outer end of the cap 258. The cap 258 comprises a first cavity of a first diameter and a second cavity of a second diameter; the first diameter desirably is larger than the first diameter so that an annular shoulder is formed on the inner wall and an annular recess and a corresponding annular shoulder is formed on the outer wall of the cap 258.

Internally, the sensor probe 6 comprises a PC board 254 and an electrical connector 256 (e.g., a RJ-45 socket) located near the tube rear end 250. Advantageously, the PC board 254 comprises a memory 257 for storing measurement characteristic of the probe 6. The connector 256 desirably is mounted on a side of the PC board 254 that faces the rubber boot 260, and the PC board 254 is attached to the cap 258 by fasteners, such as for example, by a pair of screws 252. The electrical interconnection between the memory 257 and the connector 256 is shown in FIG. 10 and will be described below.

The sensor probe 6 comprises an end plug 234 positioned near the front end 246 of the tube 248. The plug 234 includes several hollow, tube-shaped elements 232, 228, 230 of different diameters and lengths. The openings of the elements 232, 228, 230 desirably extend generally parallel to a longitudinal axis of the tube 248. Two of the openings 228, 230 are adapted to receive two rod-shaped amperometric electrodes, specifically the working electrode 150 and the counter electrode 152. The other opening is adapted to receive a plug 226.

As illustrated in FIG. 8B, the end plug 234 can also include at least one additional opening 236 for receiving a pH sensing glass electrode 238 of the optional pH sensor. Such a pH sensor can be part of the mentioned sensing system. This additional opening 236 desirably lies next to one of the openings 228 that receive one of the amperometric electrodes and to the opening 232 that receives the plug 226.

The working and counter electrodes 150, 152 desirably have similar cylindrical shapes of the same diameter and length. The length of each electrode 150, 152 is longer than the respective tubular element of the end plug 234 to extend beyond the ends of the end plug, as described below.

The electrodes 150, 152 are made of an electrically conductive material. In the illustrated embodiment, the electrodes 150, 152 are made, at least in part, of a carbon-based material, such as, for example, graphite or glassy carbon.

One wire receptacle 240, 242 is attached to each electrodes 150, 152 on an end of the respective electrode that faces the tubular body 248 of the probe 6. Each receptacle 240, 242 makes electrical contact with the respective electrode 150, 152 and receives an unshielded end of a shielded wire or conductor that connects the respective electrode 150, 152 to the connector 256 on the PC board 254, as described below. In this manner, the connector 256 located on one end of the probe 6 electrically communicates with both electrodes 150, 152 positioned on the opposite end of the probe 6 (i.e., the working end of the probe 6). As an alternative to the wire receptacles 240, 242, a conductive epoxy can be used to bond a wire to a electrode 150, 152.

The probe 6 also includes the reference electrode 154 located between the front end plug 234 and the rear cap 258 within the tubular body 248. In the illustrated embodiment, the reference electrode 154 extends from the PC board 254 toward the tube front end 246.

The reference electrode 154 is desirably made of a silver/silver chloride wire embedded in a potassium chloride (KCl) saturated gel as an electrolytic solution. The gel is preferably comprised of about 25% glycerol and about 75% KCl solution 3.5 molar with a suitable gelling agent such as methylcellulose (e.g., METHOCEL available from Dow Chemical). The gel material is schematically illustrated in FIG. 9A and 9B by a cross-hatching that includes bubbles, which is representative of a chemical solution; however, the gel desirably does not include gaseous bubbles.

The plug 226 closes the large opening in the end plug 234 to prevent an ingress of water into the electrolytic solution within the tubular body 248 of the probe 6. In the illustrated embodiment, the plug 226 desirably is made of a porous material, such as, for example, a porous glass or porous TEFLON, or wood, and functions as a membrane allowing the passage of electrons. Of course, other materials having such a characteristic (e.g., a salt bridge) can be used for the plug 226.

The other components of the sensor probe 6 such as the T-fitting 218, the adapter fitting 224, the end plug 234, the tube 248 and the cap 258 are made of suitable materials, such as, for example, but without limitation, acrylonitrile-butadienestyrene (ABS) or other polymers and plastics, which are transparent or non transparent and desirably are generally resistant to chemicals such as bromine, chlorine and hydroxides. A desirable material advantageously would also be durable, light-weight and relatively easy to manufacture. Furthermore, these components can be constructed in a variety of ways which will be well known to one skilled in the art. For example, these components can be integrally molded such as by injection molding.

Figure 9A:
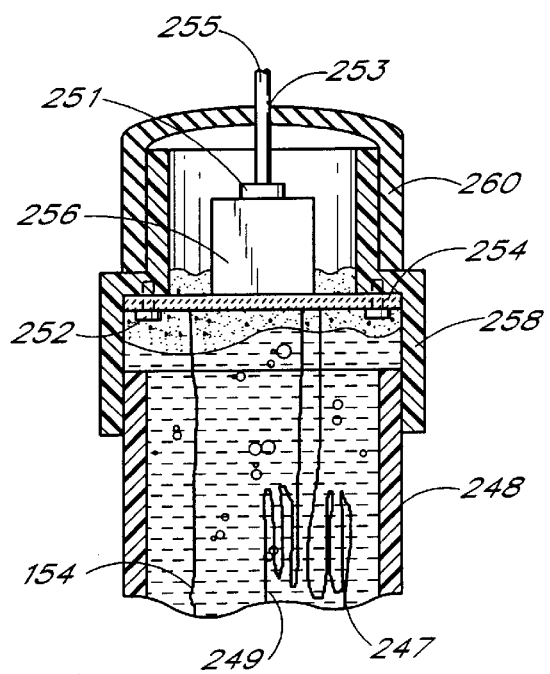
FIG. 9A is a cross-sectional view of an assembled rear portion of the sensor probe shown in FIG. 8A.
Figure 9B:
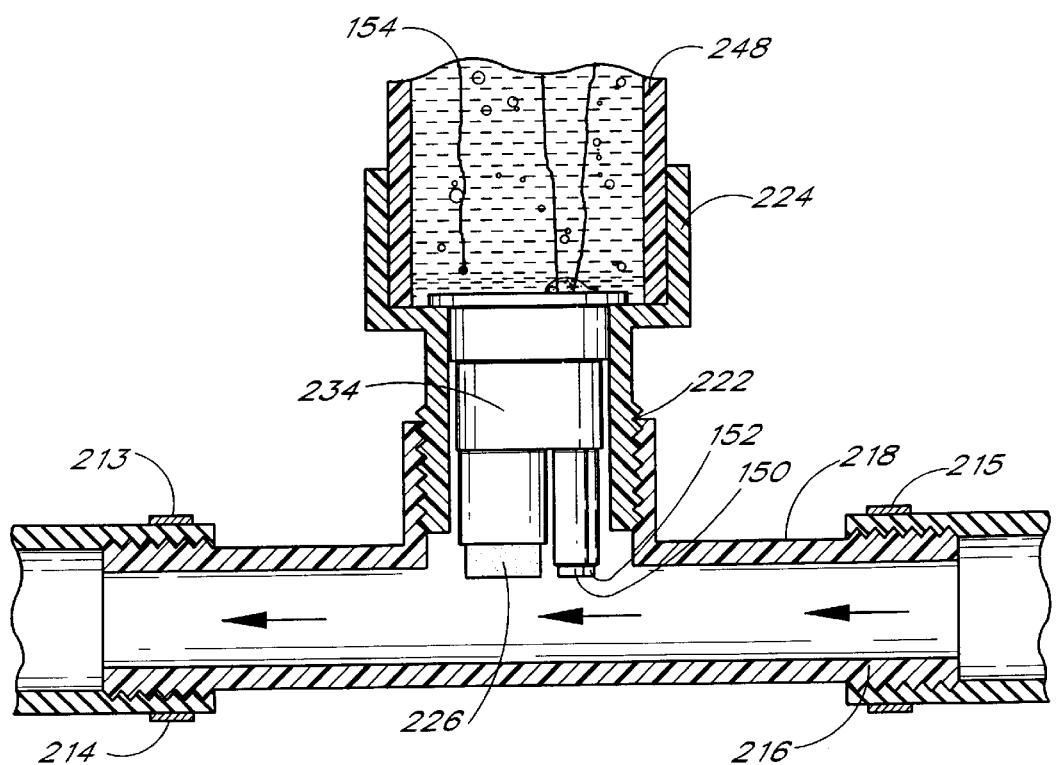
FIG. 9B is a cross-sectional view of an assembled front portion of the sensor probe shown in FIG. 8A.

FIG. 9A illustrates a rear portion of an assembled sensor probe 6; components which have been already mentioned in FIG. 8A have the same reference numerals. The cap 258 is attached to the tube 248 by a suitable adhesive or by other suitable means, such as press-fitting in combination with a sealant.

The connector 256 is mounted on a side of the PC board 254 facing the rubber boot 260; and the PC board 254 is attached to the cap 258 by the screws 252. Shielded wires 247, 249 are connected (e.g., soldered) to wire leads on a side of the board 254 that faces the tube front end 246. The wires 247, 249 extend through the gel in the tubular body 248, and as understood from FIG. 10, the opposite ends of the wires 247, 248 are connected to the electrodes 150, 152 by the wire receptacles 240, 242, respectively.

The reference electrode 154 is also attached (e.g., soldered) to a wire lead on the PC board 254. The reference electrode 154 depends from the PC board 254, through the gel in the tubular body 248, and as seen in FIG. 10, desirably terminates at a location near the end cap plug 226.

Although not illustrated, the glass pH electrode 238 (FIG. 8B), which can be contained in the end plug 234, is also connected to the PC board 254 by a third shielded wire. The wire extends through the gel in the tubular body 248 and a wire receptacle, which is similar to illustrated wire receptacles 240, 242, connects the wire to the pH electrode.

In this manner, the PC board 254 not only functions as a substrate on which to mount the electrical connector 256, the memory 257 and wire leads, to which the shielded wires 247, 249 and the reference electrode 154 are attached, but also serves to create a circuit between terminals of the connector 256 and the respective wire leads; however, any of a variety of other ways, which would be well known to those skilled in the art, can also be used to interconnect together the wires and the connector, as well as to support these components at the rear end of the sensor probe 6.

With reference to FIG. 9A, both sides of the PC board 254, the screws 252, part of the connector 256 and the wire ends are embedded or potted in epoxy or another suitable material thereby, inter alia, electrically insulating the soldering points on the PC board 254 from each other. This potted assembly also generally seals the components from the gel within the tubular body 248 as well as from ambient air and water which may enter the outer end of the cap 258.

The rubber boot 260 covers an outer end of the cap 258. Because of the rubber boot's elasticity, it slips over the cap 258 and stays there without an additional securing. The rubber boot 260 has a central opening 253 through which a data transmission line 255 is inserted and connected to the connector 256. The connection is preferably achieved by means of a RJ-45 socket connector and a corresponding jack 251 attached to the data transmission line 255. This allows easy attachment of the data transmission line 255 to the sensor probe 6 and additionally facilitates replacement of the sensor probe 6. The data transmission line 255, however, can be attached directly to the PC board 254, for example, by means of soldering.

Figure 10:
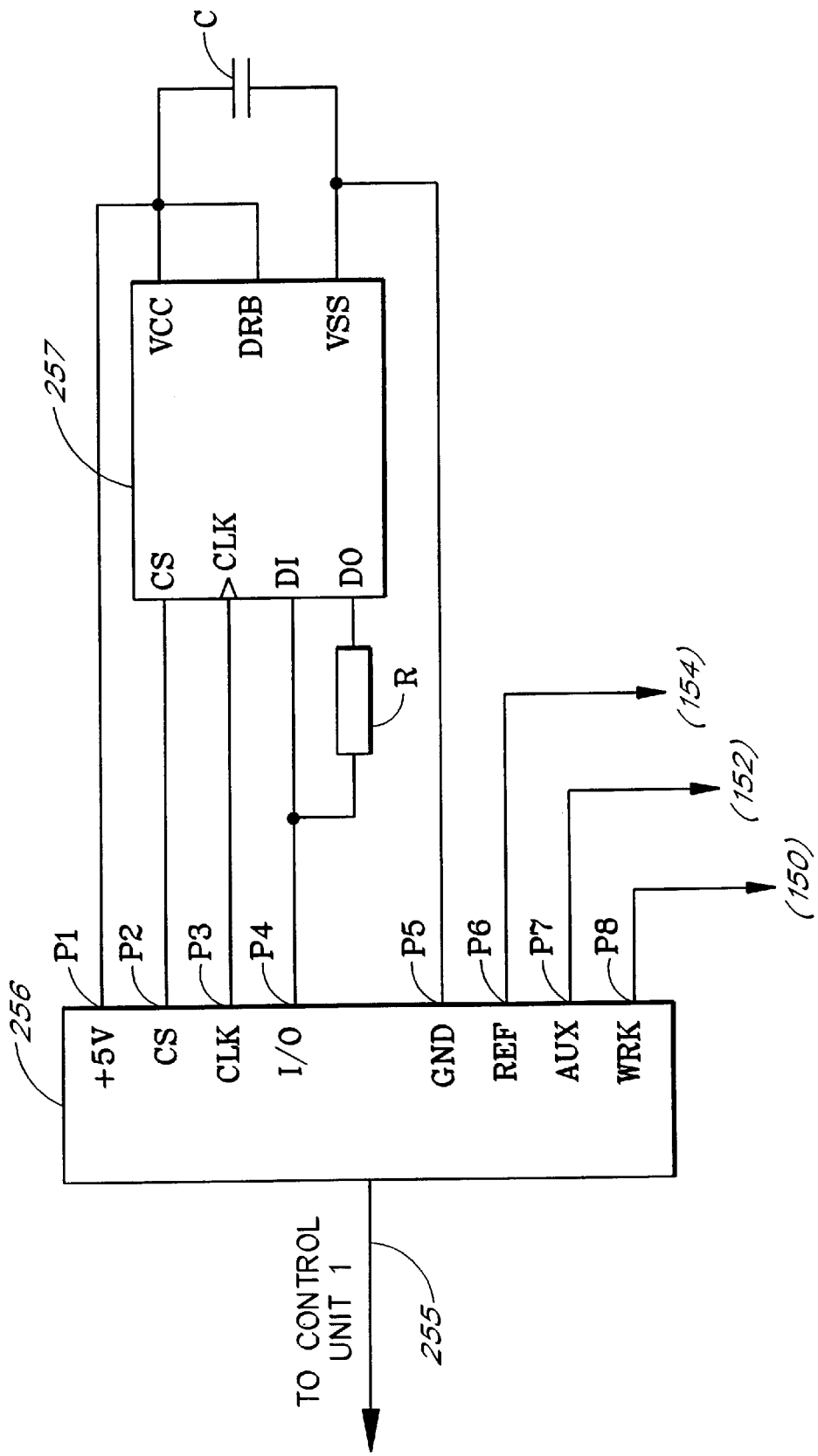
FIG. 10 is a diagram illustrating electrical interconnections between a memory device and a connector.

FIG. 10 illustrates how the memory 257 and the connector 256 are electrically interconnected. The eight pin connector 256 is attached to the data transmission line 255 which is connected to the control unit 1 shown in FIG. 1. The eight pins of the connector 256 are referenced as P1–P8. Three pins P6–P8 are connected to the electrodes 150, 152, 154 (indicated through reference numerals at the corresponding pins).

The memory 257 is preferably an electrical erasable programmable ROM (EEPROM), for example, a Microchip 93LC46 EEPROM providing 256 bytes of nonvolatile storage. The EEPROM 93LC46 has eight pins; seven pins are used in the illustrated embodiment: A chip select input CS is connected to pin P2, a clock input CLK is connected to pin P3 and a data input DI is connected to pin P4. Via a resistor R, a data output DO is also connected to pin P4. Under certain circumstances (e.g., the last bit of the address is a "1"), the microcontroller could source current to ground via the microcontroller. The resistor R limits this current to a reasonable level. To provide power to the EEPROM 257, a pin VCC is connected to pin 1 and a pin VSS is connected to pin P5 (ground). In use, a voltage of +5 volts is applied to the EEPROM 257. Between pins VCC and VSS, a capacitor C is positioned to short-cut interfering high frequency voltage components. A pin DRB is connected to pin VCC.

As explained above, the EEPROM 257 included in the probe 6 stores data specific for each probe 6; details of the specific data will be explained in connection with FIGS. 14A, 14B. The EEPROM 257 can also store data (duration of cell usage) provided by the microcontroller during operation of the system.

When the probe 6 is connected to the control unit 1 shown in FIG. 4 for the first time, the characteristic data will be read into the microcontroller memory. The EEPROM 257 and the microcontroller communicate serially and bidirectionally via a three-wire bus using a synchronous (clocked) communication protocol. During a read operation, the microcontroller sends a code word and an address to the EEPROM 257 from which data will be read. The EEPROM 257 activates the data output DO and the probe specific data is read into the microcontroller.

FIG. 9B illustrates a front portion of an assembled sensor probe 6; components which have been already mentioned in FIG. 8A have the same reference numerals. The front end 246 of the tube 248 is inserted into the adapter fitting 224 and is fixed therein by glue or another adhesive, or by other suitable means.

The adapter 224 is also fitted into the end plug 51; the openings of end plug elements 232, 228, 230 contain the two amperometric electrodes 150, 152 and the plug 226. (An additional opening 236 can contain the pH electrode 238, as illustrated in FIG. 8B). The amperometric electrodes 150, 152 and the plug 226 are glued into the openings 232, 228, 230. As illustrated in FIG. 10, the ends of the electrodes 150, 152 are exposed relative to the end plug 224 to be in contact with water flowing through the fitting 218 at the working end of the probe 6. The lengths of the electrodes 150, 152 are shorter than the lengths of the tube-shaped openings 228, 230, i.e., the electrodes 150, 152 are fully inserted into the openings 228, 230. Also, the wire receptacles 240, 242, which connect the shielded wires 247, 249 to the electrodes 150, 152, are inserted into the openings 228, 230. The rear ends of the openings 228, 230 are then sealed or potted with epoxy thereby insulating the amperometric electrodes 150, 152 from each other and from the reference electrode 154. (The pH electrode 238 can be secured and potted within the end plug 234 in a similar manner).

The threaded nipple 222 of the adapter 224 is inserted to the threaded base end opening 220 of the T-fitting 218. The side ends 216, 214 of the T-fitting 218 are each inserted into a tube which is part of the water circulation line 9 shown in FIG. 1. Hose clamps 213, 215, one at each side end 216, 214, secure hoses, which form part of the circulation line 9, to the barbed ends 214, 216 of the fitting 218.

In addition to housing the working, counter and reference electrodes 150, 152, 154 of the amperometric sensor, the probe 6 also forms a pH sensor probe. The pH sensing glass electrode 238 and the reference electrode 154 together function to form the pH sensor cell. The signal from the pH electrode is transferred via the connector 256 and the data transmission line 255 to the control unit 1 to convert the signal into a pH value which can be displayed. The pH value can also be used to control activation of a solenoid valve of a dispenser unit (not shown) to dispense a pH buffer (either in liquid or crystallized form).

Operation of the Automatic Sanitizing System

A blended salt composition comprising sodium chloride and sodium bromide is added to the spa water in which both dissolve. The salt composition comprises at least 4 percent by weight of sodium bromide and at least 75 percent by weight of sodium chloride. More preferably, the salt composition comprises at least 10 percent by weight of sodium bromide and at least 90 percent by weight of sodium chloride. The salt composition is added to the water so as to produce at least about 50 ppm sodium bromide and at least about 500 ppm sodium chloride in the resulting aqueous solution in the spa 7; desirably the aqueous solution comprises about 50 ppm to 120 ppm sodium bromide and about 1000 ppm to 1200 ppm sodium chloride. To produce concentrations of sodium bromide and sodium chloride within these ranges, the salt composition is added to the spa water at a ratio of about 1 pound of salt to every 100 gallons of water in the spa 7.

The control unit 1 in combination with the sensor probe 6 regularly measures the concentration of bromine in the spa water and controls the generator 20 to either start or stop the production of bromine.

When the control unit 1 energizes the generator 20, current flows between the negative terminal 142 and the positive terminal 144 of the power control unit 210 (see FIGS. 2 and 7). Electrical current flows through the cathode 96, through the electrolytic solution within the cell 24 and to the anodic surface of the bipolar electrode 30. The electrical current also flows through the bipolar electrode 30 to the cathodic surface of the electrode 30 and through the electrolytic solution within the cell 24 to the anode 98. Positive and negative charges are induced on the cathodic and anodic surfaces of the bipolar electrode 30, respectively. The bipolar electrode 30 thus acts as an anode on its surface facing the stationary cathode 96 and acts as a cathode on the surface facing the stationary anode 98. The power control unit 210 desirably supplies about 2.4 amps of current to the anode 98 and cathode 96, giving the anode and cathode a current density of about 0.08 amps/cm$^2$.

The control unit 1 activates via the power supply unit 2 the motor 28 when the cell 24 is energized, as discussed below. The motor 28 drives the electrode impeller 30 in a desired direction to produce a flow of water through the cell assembly 22.

The electrical potential imposed between the electrodes of the cell 24 electrolytically causes the dilute halide in the water to form pH neutral halogen, oxygen, and hydrogen, among other compounds. For instance, when the water contains a dilute solution of sodium chloride and sodium bromide, chlorine and oxygen are formed at the anode 98 and hydrogen is formed at the cathode 96 within the cell 24. The chlorine then oxidizes the bromide to elemental bromine. Once bromine is formed it can disproportionate in aqueous solutions to form hypobromous acid and a bromide anion. The bipolar electrode 30 and the anode 98 are sufficiently sized to produce chlorine, and thus bromine, at desired rate of approximately 1–2 grams per hour.

The bromine later kills algae and bacteria, and in the process is reduced back to bromide. Through this mechanism, the bromine is recycled over and over again; the bromide from the spent bromine is regenerated back so that salt rarely needs to be replenished. However, there is some loss of bromine, either caused by "degassing" (volatilization), splash-out or other such factors.

Control of the generator 20 in this manner automatically maintains the concentration of bromine within a desired range of about 2 ppm to about 6 ppm, and more preferably within the desired range of 2.5 ppm and 3.5 ppm. The control unit 1 also starts the generator 20 if usage of the spa is detected. For instance, in the illustrated embodiment, when a user activates the jets a signal is generated and input to the control unit 1 through input RA4. This allows for early initiation of bromine production so that the concentration of bromine will not significantly drop when people first enter the spa 7.

An exemplary mode of operation of the automatic sanitizing system 12 is described in connection with the flow charts illustrated in FIGS. 11, 12, 13. These flow charts, however, represent only a preferred way of operating. Those skilled in the art, however, will readily appreciate that the automatic sanitizing system 12 can be operated in any of a variety of ways.

With reference to the flow chart shown in FIG. 11A, the operation of the automatic sanitizing system 12 starts with an initialization of the system 12, as represented in operation block 801. The initialization is mainly controlled by the microcontroller 162 set to operate according to user or manufacturer parameters. Such parameters include, for example, the size of the spa body, an estimation of the amount of usage or usage factor, or other such parameters. These parameters allow the control unit 1, and more specifically the microcontroller 162, to determine the duty cycle time. The initialization may also include reading probe specific data from the EEPROM 257 located within the end portion of the probe 6.

The control system from this point forward operates through a generally continual series of duty cycles until the control system is taken off line (i.e., turned off). The following describes the control operation through a single duty cycle. It is to be understood that the same sequence of steps desirably is performed in each duty cycle. Thus, the description herein of one will be understood as a universal description of all of the duty cycles preformed by the control system.

The duty cycle begins by turning off (i.e., deenergizing) the cell 24, if active, and turning on the motor 28, as represented in operation block 802. This is specifically accomplished by applying the corresponding control signals DATA, CLK and RST to the power supply unit 2. The mentioned turning "off" or "on" of the motor 28 or cell 24, as it will be understood by those skilled in the art, means that a voltage or a current of sufficiently high amount to enable operation is applied or cut off. This can be achieved through a variety of means, for example, opening or closing an electrical switch and thereby connecting or disconnecting the motor 28 or cell 24 to a voltage or current source; or operating an output of an integrated circuit between a high or low state.

The initial act of starting the pump motor 28 of the generator 20 (operation block 802) represents the start of a measurement cycle during which the sanitizing agent (e.g., bromine) concentration is determined. The motor 28 is active for one minute and desirably circulates about 1.5 gallons per minute (5.775 liter per minute), as represented in operation block 803. As long as one minute has not elapsed, the system checks for motor 28 faults, as represented in block 812. The detection units 208, 212 (FIG. 7) provide the signals "motor current high", "no motor current", "cell current low" and "no cell current". Each of these signals can be input to the microcontroller input RA4 for further processing. In case such a signal is received, i.e., a specific state or fault has been detected (decision block 813), a fault code is displayed, as represented in operation block 814. This fault code informs the user of the fact that a fault has been detected and of the kind of fault, for example, no cell current. As a consequence of the detected fault, the microcontroller 162 shuts down the power supply for the cell 24, as represented in operation block 815. Next, the system falls into an idle mode, as represented in operation block 816, until the user repairs and resets the system.

In the preferred embodiment of the present invention, the actual measurement of the bromine concentration in the spa water, as represented in operation block 808, takes place after one minute has elapsed and if no faults are detected. The required reference voltage for sensing bromine (+300 mV) is applied to the sensor probe 6 during one minute. The microcontroller 162 initiates a code word to be applied to the multiplexer control inputs A, B to switch one selected reference voltage to the output Y. This voltage (+300 mV) is then applied to the input 168 of the potentiostat 156 and fed to the counter electrode 152 of the sensor probe 6 via the multiplexer 189 ("input" X, "output" X0). The measurements are ignored until the end of the one minute cycle. At the end of one minute, the microcontroller 162 takes 256 measurements and averages them. Each measurement results in a current indicative of the concentration of bromine in the spa water; the current is converted to a voltage by the I/V converter 174 of the potentiostat 156 and fed to the microcontroller 162 which processes the sensor probe signal, inter alia, through the internal A/D converter.

In the preferred embodiment of the control unit 1, positive and negative voltages originating from the sensor probe signal can be processed:

If the voltage is positive, a positive voltage (output 158a) is fed to the input AN0. The positive voltage (output 158b) is also fed to the inverter 193 which outputs a negative voltage that is fed to the input AN1. This negative voltage, however, will not be processed.

If the voltage is negative, a negative voltage (output 158a) is fed to the input AN0, but will not be processed. The negative voltage (output 158b) fed to the inverter 193 is converted into a positive voltage and fed to input AN1.

After determining the bromine concentration, the microcontroller 162 again initiates the application of the required reference voltage (+300 mV) to the sensor probe operation working electrode 150; the reference voltage is also measured, as represented in block 804. The measurement of the reference voltage is made by the microcontroller 162 which receives the selected reference voltage from the output X of the multiplexer 194. Since the output Y of the multiplexer 194 is directly connected the inputs X0, X1, X2, and via the inverter 183 to the input X3, by selecting one reference voltage a corresponding input X0–X3 is addressed and switched through to the output X. If the reference voltage is not equal to +300 mV, as represented in decision block 805, the system initiates a fault code which is displayed (operation block 814) and the idle mode is begun (operation blocks 815, 816). In such a case, the previously taken bromine measurements are dropped.

If the applied reference voltage equals +300 mV, the system measures the negative power supply, for example, –4.3 volts for the potentiostat 156, as represented in operation block 806. The microcontroller 162 measures the voltage output from the voltage control unit 192 connected to the input AN4. A failure of this requirement (see decision block 807) also leads to the display of a fault code (operation block 814) and to the subsequent shut down (operation block 815) of the cell 24 and the start of the idle mode (operation block 816).

It should be understood that the described voltage measurements (operation blocks 804, 806) are optional; however, these diagnostic steps insure that the system is operating properly. For instance, loss of the negative power supply of –4.3 volts to the operational amplifier devices of the potentiostat 156 may falsely indicate that the concentration of bromine in the spa water is too low, for example, zero.

The measurement of bromine is followed by an optional measurement of the spa water temperature, as represented by operation block 809. At this step, the microcontroller 162 receives a signal from the communication interface 187 which is connected to the temperature sensor 13. The microcontroller 162 uses the temperature measurements to eventually correct the current measurements for changing water temperature caused by, for example, intense solar irradiation or heating. As noted above, the temperature measurement is optional depending on the requirements regarding the accuracy of the bromine readings and the resulting control of the generator 20. In the illustrated embodiment of the automatic sanitizing system 12, the microcontroller 162 can be programmed to use temperature readings or to perform the control without such readings.

After this temperature measurement, the microcontroller 162, via the power supply unit 2, turns off the motor 28, as represented in operation block 810, after it has been active for one minute. This action constitutes the end of the measurement cycle. Advantageously, during the measurement cycle the cell 24 is turned off, i.e. no voltage is applied and consequently no electrolysis takes place.

The microcontroller 162 uses the measured current flowing between the working electrode 150 and the counter electrode 152 as a control parameter during a control cycle, as represented by operation block 811; this control cycle will be explained below in connection with FIG. 12.

Figure 11B:
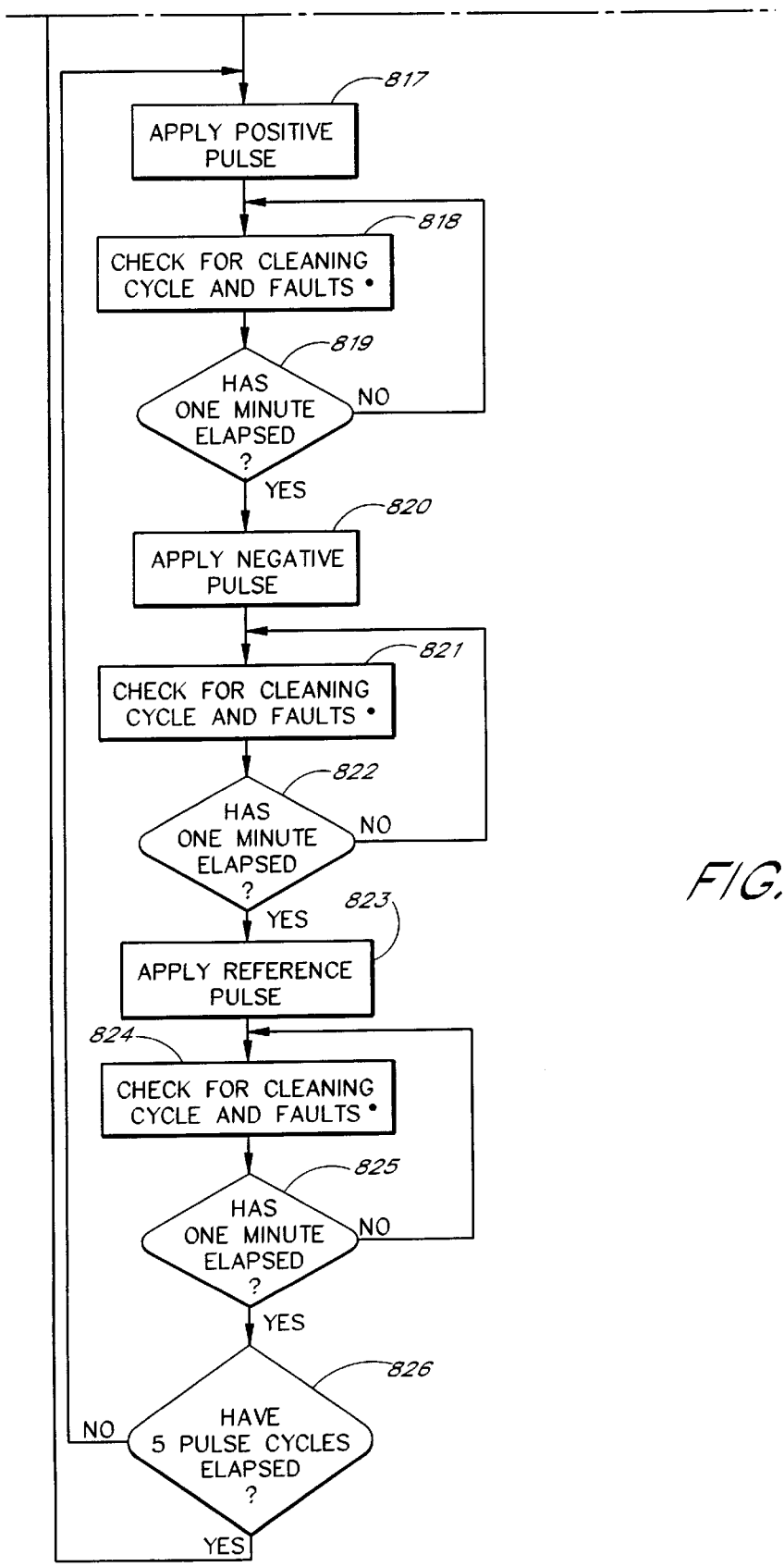

A cleaning cycle, as represented by blocks 817–826 in FIG. 11B, is employed to clean the sensor probe 6. The cleanness of the exposed electrodes 150, 152 of the sensor probe 6 directly influences the reliability of the current measurements because the chemical reactions occur at the surfaces of these electrodes 150, 152. Any deposition of salt and/or algae alters the electrical characteristic of the electrodes 150, 152. Therefore, adequate cleaning helps to achieve reliable current measurements and subsequently reliable bromine concentration readings. Also, as described above, the positioning of the sensor probe 6 downstream of the generator 20, as shown in FIG. 1, helps to minimize algae deposition.

The cleaning cycle desirably starts after the control cycle. As represented by operation block 817 and decision block 819, a positive potential of +1 volt is initially applied during the cleaning cycle between the working electrode 150 and the counter electrode 152 for one minute. Secondly, as represented by operation block 820 and decision block 822, a negative potential of −100 millivolts is applied between the working electrode 150 and the counter electrode 152, also for one minute. And thirdly, as represented by operation block 823 and decision block 825, a positive potential of +300 mV is applied between the working electrode 150 and the counter electrode 152 for one minute. This sequence is repeated five times, as represented by decision block 826; no measurements are taken during this fifteen minute cycle. The application of the different voltages is controlled by the microcontroller 162 which controls the multiplexer 194 (code words applied to control inputs A, B) to alternatingly switch different voltages from the inputs Y0–Y3 to the output Y. Those skilled in the art will recognize that other voltage sequences can be applied to clean the electrodes of the sensor probe 6.

The described cleaning cycle generates an oxidizing species and thereby cleans the electrodes of the sensor probe 6 of any salt build-up. After five sequences have elapsed, the next duty cycle begins (at operation block 802).

Each time one of the three different potentials is applied, a check cycle starts, as represented by operation blocks 818, 821 and 824. One example of such a check cycle is explained in connection with the flow chart shown in FIG. 13, which will be described below.

Figure 12:
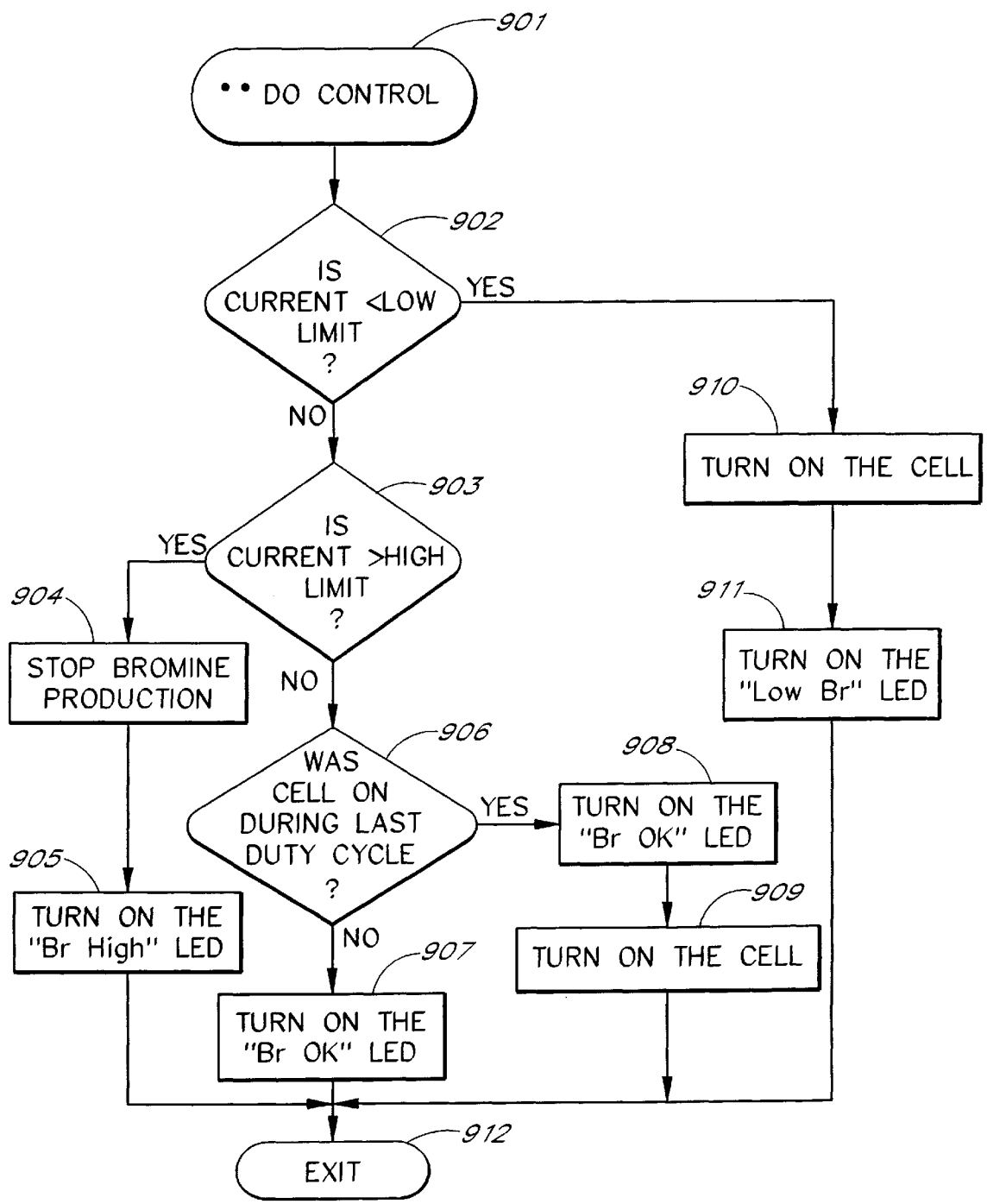
FIG. 12 is a flowchart illustrating a control cycle applied in the automatic sanitizing system.

As noted above, the measurement cycle is followed by a control cycle (block 811) which is illustrated by the flow chart shown in FIG. 12. The control cycle, as represented by blocks 901–912, is described using the current flowing between the working electrode 150 and the counter electrode 152 as a control parameter since the measured current directly correlates with concentration of the measured species (e.g., bromine), although the potentiostat 156 outputs a voltage. However, those skilled in the art will recognize that the control cycle can be equally described using the voltage output from the potentiostat 156 or a digital value calculated by the microprocessor 162.

As described above, the microcontroller 162 receives the sensor probe signal, which corresponds to the current, for internal processing. If the current is above the upper threshold, as represented by decision blocks 902 and 903, the microcontroller 162 outputs control signals that are fed to the power supply unit 2 to stop the production of bromine by turning off the cell 24, as represented by operation block 904. The upper threshold limit is stored in the memory 190 and retrieved by the microcontroller 162 during this control cycle. Additionally, the microcontroller 162 controls the display 198, as represented by operation block 905, indicating that the concentration of bromine is above the desired concentration of, for example, 3.5 ppm, and that the cell 24 has been turned off. The motor 28 and the cell 24 will be shut down for 15 minutes. After that time, the concentration of bromine is measured again during the next duty cycle. The cleaning cycle desirably runs during this down time; however, the cleaning cycle need not be nested within the control cycle as these cycles are not interdependent.

If the current is below the lower threshold, as represented by decision block 902, the microcontroller 162 outputs signals that the power supply unit 2 receives to start production of bromine by turning on the cell 24, as represented by operation block 910. Like the upper threshold limit, the lower threshold limit is stored in memory 190 and is retrieved by the microcontroller 162 during this portion of the control cycle. Also, the microcontroller 162 controls the display 198, as represented by operation block 911, indicating that the concentration of bromine is below the desired concentration, for example, 2.5 ppm, and that the cell 24 has been turned on. The cell 24 desirably runs for 15 minutes.

The production of bromine also begins when the current is between the upper and lower threshold and the cell 24 was activated during the immediately preceding duty cycle, as represented by decision blocks 902, 903, and 906 and operation block 909. Also, the microcontroller 162 controls the display 198 to indicate that the concentration of bromine is within the desired range, as represented by operation block 908.

If the current is between the upper and lower threshold and the system was not turned on during the last duty cycle, as represented by decision blocks 902, 903, 906, the microcontroller 162 controls the display 198 to indicate that the concentration of bromine is within the desired range, as represented in operation block 907.

The foregoing control mode of the cell 24 insures that when the bromine concentration falls below a desired level (e.g., 2.5 ppm), the control system will raise the concentration level up to or slightly more than a desired upper level (e.g., 3.5 ppm). However, once a concentration level near the upper limit is reached, the system will maintain the cell 24 in an inactive state while the bromine concentration level falls through the desired preset range (e.g., 3.5 ppm to 2.5 ppm). In this manner, the control system does not constantly activate the cell 24 and cause the bromine concentration level to fluctuate above and below only one of the preset range limits.

Figure 13:
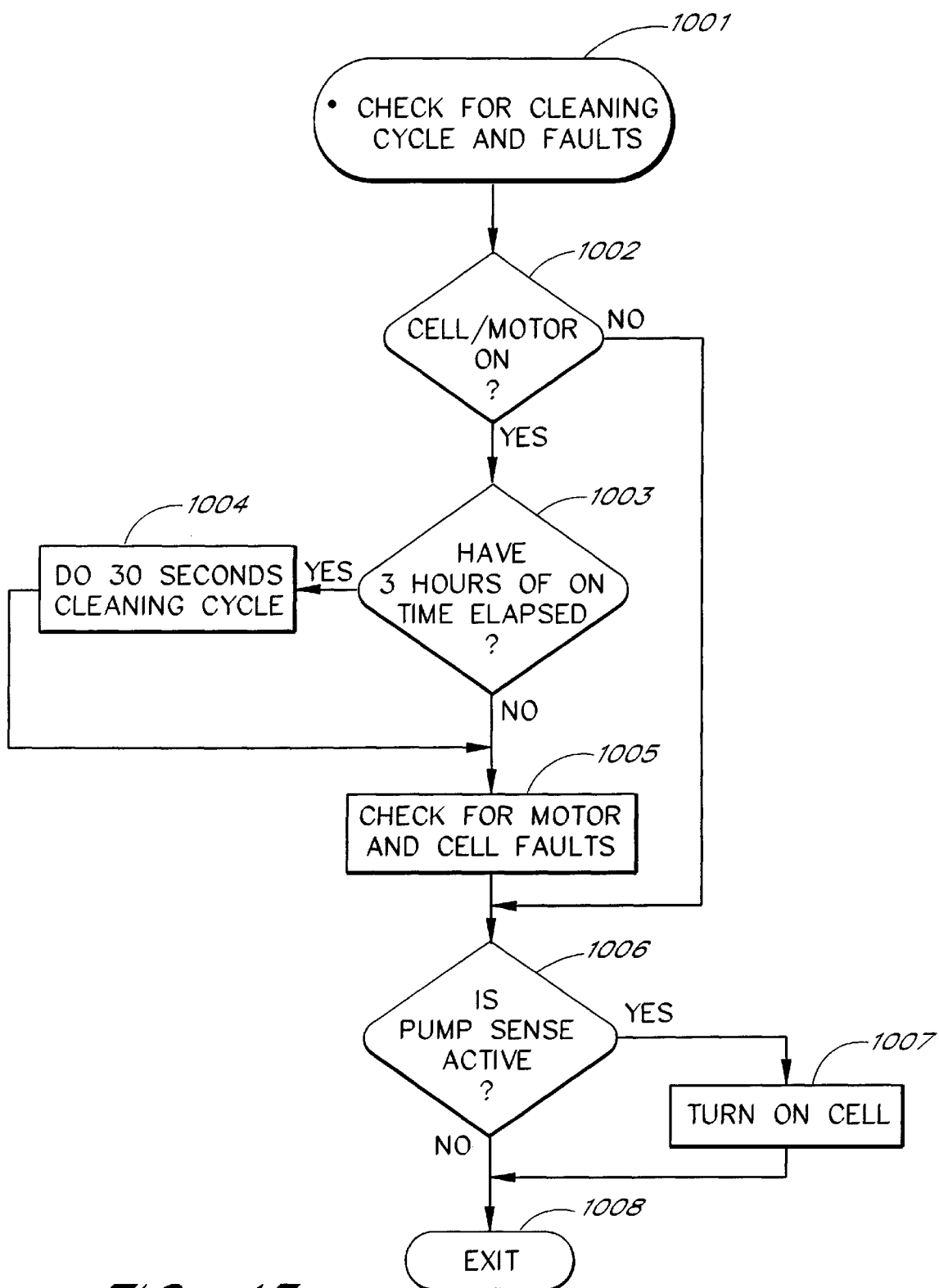
FIG. 13 is a flowchart illustrating a cleaning cycle applied in the automatic sanitizing system.

A flow chart of the check cycle (FIG. 11, blocks 818, 821, 824) is shown in FIG. 13. When the cell 24 and motor 28 have been active for a cumulative period of three hours, as represented by decision blocks 1002, 1003, the electrodes of the cell 24 will be cleaned, as represented by operation block 1004. As described above, the memory 190 stores the duration for which the motor 28 and the cell 24 have been operated. The microcontroller 162 inputs data into this memory 190 and retrieves data from it, for example to start the cleaning cycle after a preset operation time. Cleaning is, inter alia, required to remove scale from the electrodes and thereby maintaining operability of the generator 20. There are several ways to remove scale, as described below.

The control unit 1 (i.e., the microcontroller 162) can cause the motor 28 to undergo rapid rotational directional reversals several times at regular intervals during the check cycle or to periodically reverse the rotational direction of the impeller 30 during its operational cycle. For instance, during each scale removal sequence, the control unit 1 causes the motor 28 to rotate the electrode impeller 30 in one direction for 15 seconds, then reversed to rotate the electrode impeller 30 in an opposite direction for another 15 seconds. This reversal is repeated six times during the scale removal sequence.

Rapid reversals of the rotational direction of the bipolar electrode 30 have been found to cause scale deposits within the cell 24 to be quickly removed. The rapid reversals in the bipolar electrode's rotational direction create rapid water flow reversals relative to the stationary cathode 96. These water flow reversals also are present relative to the lower surface of the bipolar electrode 30 by virtue of the stationary baffle 122. Such flow reversals generate turbulence adjacent the cathodic surfaces within the cell 24 to swirl and knock off scale growth before it can affect the efficiency of the cell 24.

The ability of the cathode plate 102 to move toward the rotary electrode 30 also can be used for scale removal. With reference to FIG. 2, the spring 110 allows the cathode plate 102 to be displaced in an axial direction within the cell 24. The cathode plate 102 is mounted at an optimum spacing with respect to the bipolar electrode 30 for efficient electrolysis with the spring 110 in a relaxed, undeflected state. As the pressure within the cell 24 changes, the cathode plate 102 is displaced toward the electrode 30.

During the cell cleaning step (operation block 1004), the motor 28 drives the electrode impeller 30 for about 30 seconds at a high rate of speed to generate a lower pressure at its surface facing the cathode 96, thus urging the cathode plate 102 toward the bipolar electrode 30 and against the bias of the spring 110. Excessive scale buildup on the cathode plate 102 will contact the vanes 130 or tabs 128, thus cleaning the cell 24 automatically. As the motor 28 slows down, the cathode plate 102 returns to the optimum spacing from the electrode 30 for efficient electrolysis. This high speed cleaning cycle can be easily accomplished with a minimum of electric circuitry.

This cleansing is done each time the cell 24 and the motor 28 have been operated for three hours.

If three hours have not yet elapsed and the cell 24 and the motor 28 are active, as represented by blocks 1002, 1003, or the cleaning has been done, as represented by block 1004, the current to the motor 28 and the current to the cell 24 are checked, as represented by block 1005, which provide important information for maintenance. For instance, no cell current or no pump current can indicate disconnection from the power supply.

The control unit 1 in combination with the power supply unit 2 monitor the current draw of the motor 28 of the generator 20. As scale builds up on the electrode surfaces within the cell 24, the motor 28 experiences more drag and additional loading. This added load translates into a current increase through the motor 28 which is monitored. The control unit 1 may alternatively implement a descaling cycle when the current increases by a preset percentage, such as, for example, a 20% increase from normal current draw of the motor 28.

Sensing the motor current will also indicate a problem with loss of fluid prime within the generator 20. If there is no fluid in the cell assembly 22, the motor 38 will experience a dramatic reduction in load and associated decrease in current flow. A significant drop of motor current, such as, for example, 50% or greater, may be indicative of a loss of prime. In such a case, the control unit 1 should deenergize the generator 20. Occasionally, massive scale buildup followed by a cleaning cycle will dislodge a large quantity of scale leading to a clog which can "seize" small motors. In this situation, the control unit 1 can sense the rapid increase in current draw by the motor 28 and trigger a rapid series of motor reversals to dislodge the clog.

In all of these cases, the current through the motor 28 is detected in conventional ways and this information is used by the control unit 1 to instigate the various responses described. The specific circuit diagrams and logic used and briefly described above are shown in a black-box manner in FIG. 7 and believed within the scope of experience of one skilled in the motor feedback and control art.

The current through the cell 24 may also be monitored as a means of determining the timing and duration of cell operation. More specifically, as scale builds up, the cell current will decrease. In this situation, the control unit 1 will run the cell 24 for a longer period than normal to compensate for the reduced halogen concentration generated by a less than efficient, or scaled cell. Optionally, the operation of the cell 24 may coincide with the operation of the spa jet booster pump or air injection blower to increase the halogen generation in periods of increased need.

An increased need due to spa usage can also be detected during the check cycle, as represented by block 1006. The automatic sanitizing system 12 is adapted to receive, via the shift register 207 shown in FIG. 7, a signal indicating that the spa jets are active, i.e., the spa 7 is used. If a usage is detected, the microcontroller 162 starts producing bromine by activating the cell 24, as represented by block 1007. It is optional, if the production of bromine is immediately started after the usage is detected or if a certain time delay of a few minutes is applied.

Diagnostic System

In a preferred embodiment of the automatic sanitizing system 12, the proper operation of the sensor probe 6 can be monitored. This is achieved through the diagnostic system 166 included in the control unit 1, as shown in FIG. 5. The diagnostic system includes a diagnostic unit and a voltage sensor as described below. The diagnostic system 166 determines if the conductivity between the working electrode 150 and the reference electrode 154 decreases; i.e., if the conductivity through the sensor probe plug 226 (FIG. 8A) decreases.

For this determination, a low or medium frequency signal in the range of 4 kHz to 10 kHz is used; preferably it is a 5.7 kHz square wave signal with no DC component which is applied to a voltage divider. The microcontroller 162 outputs at its output RC2 a 5.7 kHz square wave signal having a 2 volts DC component which is fed to a capacitor (not shown) to block the 2 volts DC component. If the square wave signal is to be applied, the microcontroller 162 energizes the solenoid 181 that operates the switch 181*a* to connect the working electrode 150 to the output RC2 via the capacitor. The working electrode 150 receives the square wave signal. Furthermore, the solenoid 181 operates the switch 181*b* to connect the reference electrode 154 via the input Y1 of the multiplexer 189 to the diagnostic system 166. Through this, a voltage divider is created consisting of an impedance between the working electrode 150 and the reference electrode 154, and an internal resistor which is part of the diagnostic system 166. This results in a sensible voltage across the internal resistor having a square wave function, its magnitude depends on the magnitude of inter-electrode impedance. The resulting voltage is rectified using a precision full-wave rectifier. An output of the rectifier is connected to a capacitor to filter any AC component from the resulting voltage, and to the input AN3 of the microcontroller 162. A change in the inter-electrode impedance causes a change in the DC voltage fed to the internal A/D converter of the microcontroller 162 and can indicate that the plug 226 is clogged, or that the working electrode 150 surface has plated out, or that the salt concentration in the spa water is too low. In such a case, the microcontroller 162 can display a code indicating that service is required and/or initiate counter measures, such as resetting the sensor probe 6.

Operation of the Potentiostat

The operation of the potentiostat 156, as shown in FIGS. 5, 6 is best understood by keeping in mind that an operational amplifier reacts in the manner required to maintain zero potential difference between its inputs. Thus, a stable state for a loop consisting of the follower 170 and the inverter 172 corresponds to the output of follower 170 being equal in magnitude, but opposite in polarity to the applied voltage on input 168. Since the follower 170 is in the follower configuration, its output must equal minus the applied voltage relative to ground potential. Because the reference electrode 154 is maintained at minus the applied voltage and the working electrode 150 at zero volts, the potential of the working electrode 150 relative to the reference electrode 154 is maintained at the applied voltage.

The operational amplifiers 170, 172, 174 are advantageously provided with an asymmetric power supply of +5 volts and a negative potential in the range of −4.5 volts and −4.2 volts, preferably −4.3 volts. The +5 volts potential is provided by a known voltage regulator (see FIG. 15) and the −4.3 volts potential is provided by a combination of a voltage regulator for −5 volts (see FIG. 15), a 4.3 volts zener diode and a serial 33 Ohm resistor. Such a negative potential prevents the operational amplifiers 170, 172, 174 from permanently saturating when the potentiostat 156 operates in a pulsed mode, as used during the cleaning cycle. The reduction of the negative power supply from the usually applied −5 volts to −4.3 volts provides recovery of the operational amplifiers 170, 172, 174 in short time, typically faster than 30 seconds.

In operation, i.e., when a voltage determined by the electrochemical potential of bromine is applied to the sensor probe 6, a current flowing between the counter electrode 152 and the working electrode 150 is output from the sensor probe 6 and fed to such a potentiostat 156.

In case that a species other than bromine is to be sensed, the control unit 1 applies a voltage determined by the electrochemical potential of that species. This voltage is also provided by the reference voltage unit 160 which comprises several individual voltage units, e.g., formed by voltage dividers connected to +5 volts or −5 volts. Alternatively, a reference voltage can be generated with a Zener diode and a serial resistor, as well known in the art.

The reference voltage unit 160 used in the preferred embodiment of the invention can be adapted to output the voltage required for the species. Such an adaption can be done, for example, by changing an existing voltage divider or by adding an additional voltage divider. The additional voltage divider can be pre-installed so that only a connection to a reference voltage unit 160 output is necessary. In the preferred embodiment, the reference voltage unit 160 provides, for example, −100 millivolts, 300 millivolts, 1 volt and 0 volt.

Figure 14A:
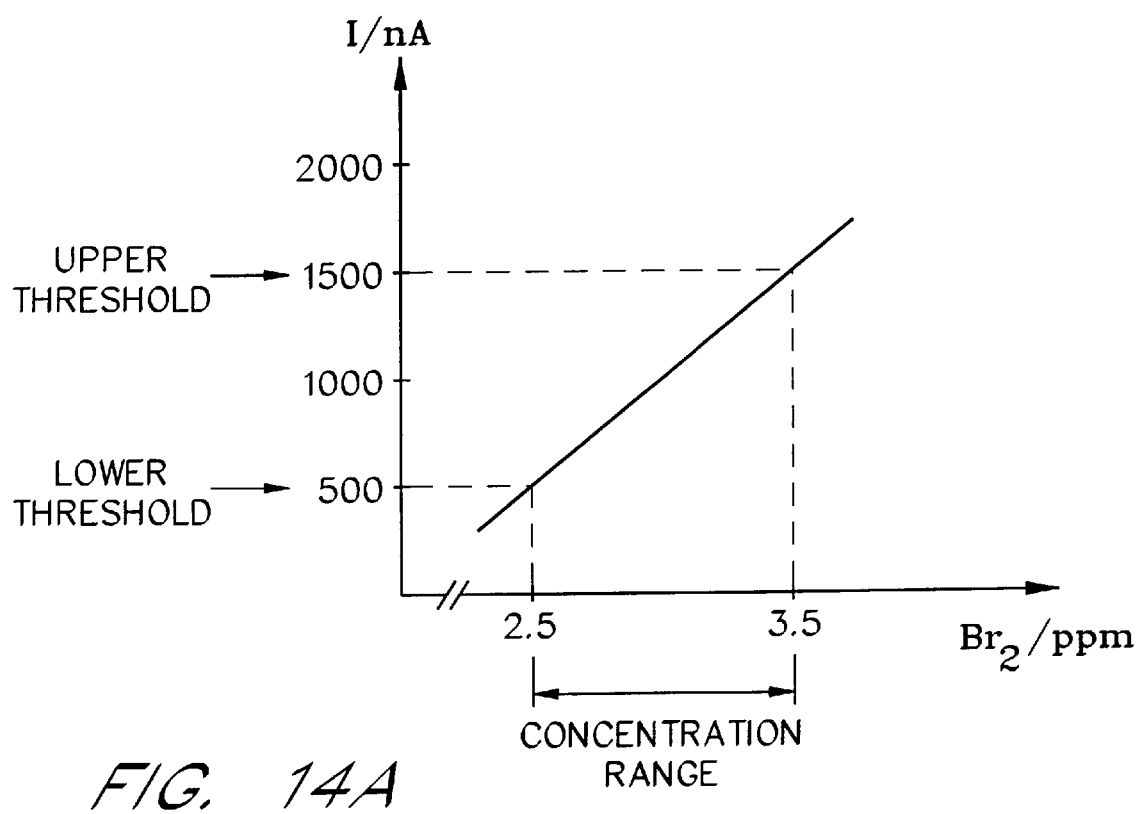
FIG. 14A is a graph showing a sensor probe current response as a function of bromine concentration.
Figure 14B:
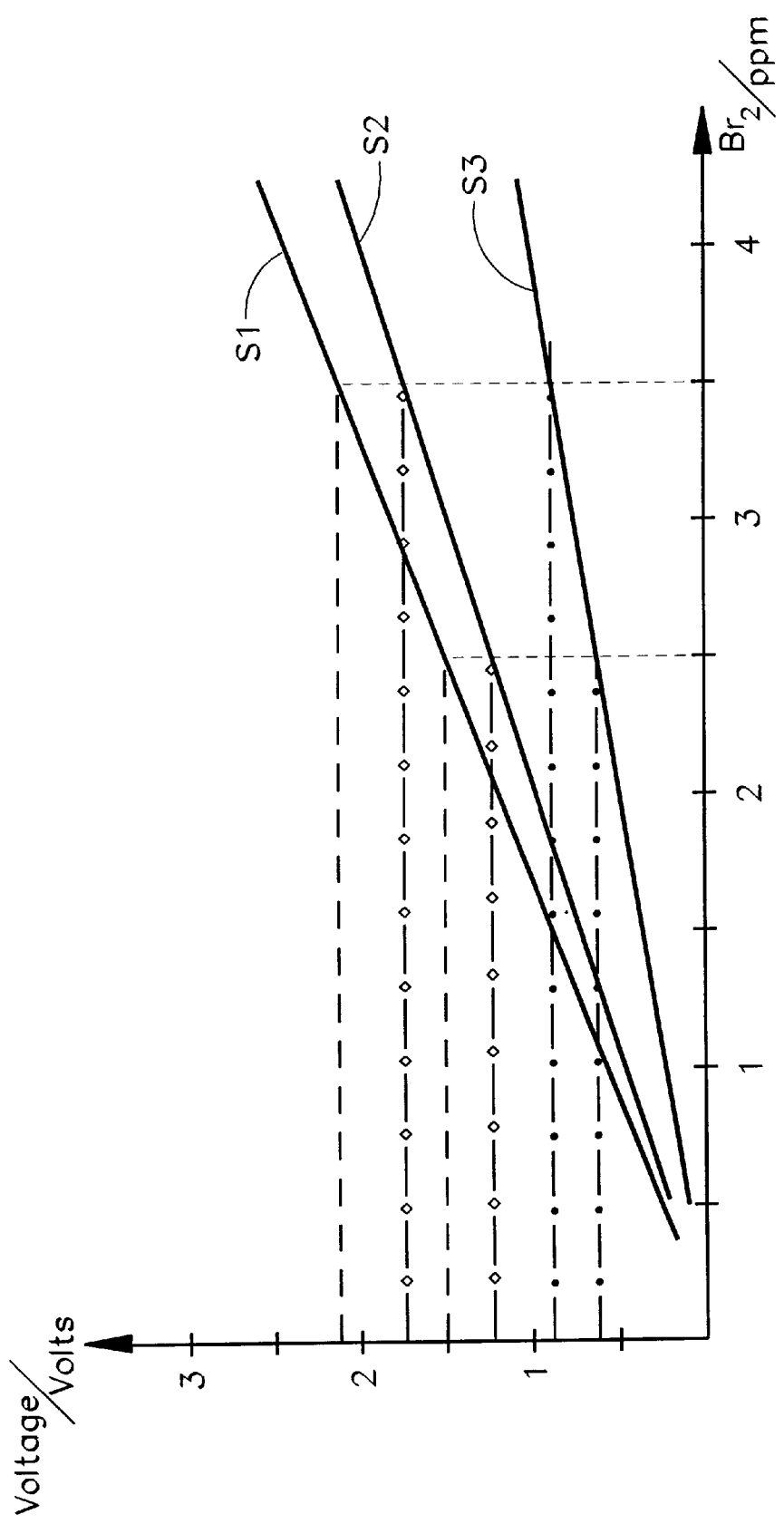
FIG. 14B is a graph showing voltage responses of different sensor probes as a function of bromine concentration.

In FIG. 14A, a graph is shown to illustrate the sensor probe 6 current response as a function of the bromine concentration. Illustrated is the linear current response in nanoampere (I/nA) for the desired bromine concentration ($Br_2$/ppm) in the range of about 2.5 ppm and about 3.5 ppm. For the current response, a lower and an upper threshold are defined. In the preferred embodiment of the present invention, the lower threshold, for example, set at 1100 nA, indicates that the bromine concentration has reached 2.5 ppm and the upper threshold, for example, at 1500 nA, indicates that the bromine concentration has reached 3.5 ppm.

In order to achieve the linear current response as a function of bromine concentration (FIG. 14A), it has been determined that the concentration of bromide should be at least 50 ppm. It is believed that a bromine concentration at or above this level will cause substantially all of the hypobromous acid to react with the bromide and produce bromine in reaching an equilibrium state. As a result, the concentration of bromine is increased to a level sufficient to produce a linear current response. The particular current response of a specific probe 6 is unique. That is, each probe 6 produces a current response at a certain bromine concentration level which is very likely different from a current response generated by another probe at the same bromine concentration level. FIG. 14B shows a graph illustrating exemplary voltage responses of three probes as a function of the bromine concentration level ($Br_2$/ppm). The voltage response is proportional to the current response (see FIG. 14A) and is generated through a current-to-voltage conversion within the potentiostat. Each voltage response S1, S2, S3 has a different slope, for example, the slope of the voltage response S1 of the first probe is about 1.6 ppm/volt, the slope of the voltage response S2 of the second probe is about 2 ppm/volt and the slope of the voltage response S3 of the third probe is about 4 ppm/volt. Thus, as used herein in connection with the exemplary embodiment, "output voltage response" means the voltage converted and output by the potentiostat in connection with a current response measured by the amperometric sensor probe.

As discussed above, the desired concentration range for bromine is between 2.5 ppm and 3.5 ppm, and upper and lower thresholds for the output voltage response are defined. Thus, in the present examples, the upper and lower thresholds (dashed lines) for the first probe (output voltage response S1) are about 2.1 volts and about 1.5 volts, respectively. The upper and lower thresholds (dotted lines) for the second probe (output voltage response S2) are about 1.8 volts and 1.3 volts, respectively. The upper and lower thresholds (dotted lines) for the third probe (output voltage response 53) are about 0.8 volts and about 0.6 volts, respectively.

This indicates that an isolated output voltage reading without information about the output voltage response characteristic of a specific probe is of little use and may be misleading. For example, an output voltage reading of 2 volts can indicate for the second probe (output voltage response S2) that the bromine concentration is too high. However, for the first probe (output voltage response S1) the output voltage reading of 2 volts indicates that the bromine concentration is still within the desired range.

The control unit 1 (FIG. 4), therefore, desirably receives information about the output voltage response characteristic of the specific probe to which it is connected. The output voltage response of a probe desirably is determined after manufacture of the probe and stored as a look-up table in the EEPROM 257. The EEPROM 257 can store other measurement characteristics in addition or in the alternative to providing an output voltage response that is unique to a particular probe. For instance, such measurement characteristics associated with a particular probe can include, for example, but without limitation, data related to measured electrochemical potential (e.g., ionic or oxidation reduction potential) versus concentration, measured current flow versus concentration, and measured conductivity versus concentration. If necessary, the EEPROM 257 can also store an offset value or several data points in the event a batch of probes is nonlinear to account for background current, as well as decay time (e.g., time necessary for probe to stabilize within a sample before measurement taken). The EEPROM 257 thus can store such uniquely specific data with the particular sensor probe 6.

The measurement characteristic of the probe desirably is determined empirically by testing the probe in a known environment. For example, in the illustrated embodiment, a first output voltage response is measured using a solution of a known first bromine concentration (e.g., 2.5 ppm). At this concentration, the output voltage is measured to provide one data point of the output voltage response table. Through interpolation and extrapolation, further points can be determined. For instance, by assuming that the output voltage is zero at a bromine concentration of 0 ppm, a second data point of the output voltage response is available. Then by assuming a model for the output voltage response in the concentration range between 0 ppm and known first concentration level (e.g., 2.5 ppm), the output voltage response between the measured and assumed points can be interpolated. In a preferred embodiment, a linear model is used; however, other models can also be used. In addition, a solution of a known second bromine concentration, or several other solutions having known bromine concentrations, can be used to determine further data points of the output voltage response. The interpolated output voltage response desirably is then discretized for discrete concentration values, and then stored in the look-up table in the EEPROM 257.

The output voltage response can also be calculated by extrapolation using the assumed model for output voltage response and the measured and assumed data points. The extrapolated output voltage response can then be discretized in a variety of output voltage/$Br_2$ pairs and stored in the EEPROM 257 in the look-up table.

The stored output voltage response can be read into the microcontroller, as explained above in connection with FIG. 10. In use, when the microcontroller receives a measured voltage, the microcontroller can associate this voltage with a stored output voltage/$Br_2$ pair to determine accurately the bromine concentration.

The EEPROM 257 can also store data specific to the probe 6, in addition to or in the alternative to a measurement characteristic (e.g., output voltage response). For instance, the EEPROM 257 can store information relating to the manufacturer of the sensor probe, its serial number or possible other data, which allow identification and interoperation of the probe with the automatic sanitizing system illustrated in FIG. 1A. For instance, such interoperational data can include a specific hand-shake protocol.

Storing measurement characteristic data, and possible other information, of a probe in an EEPROM included in the probe, eliminates the need for normalization or calibration when a probe is initialized or replaced in the system. An additional advantage is that inexpensive materials (carbon based materials) can be used for the electrodes instead of platinum or gold electrodes, which produce more uniform measurement responses from probe to probe. The non-uniform measurement responses uniquely associated with probes including less expensive electrodes, can be stored with and accompany the electrode. However, it is understood that although the present sensor probe includes a memory device, the automated sanitizing system will operate acceptably when conventional methods for normalization or calibration are used instead of storing characteristic data of the sensor probe in the probe's memory.

Figure 15:
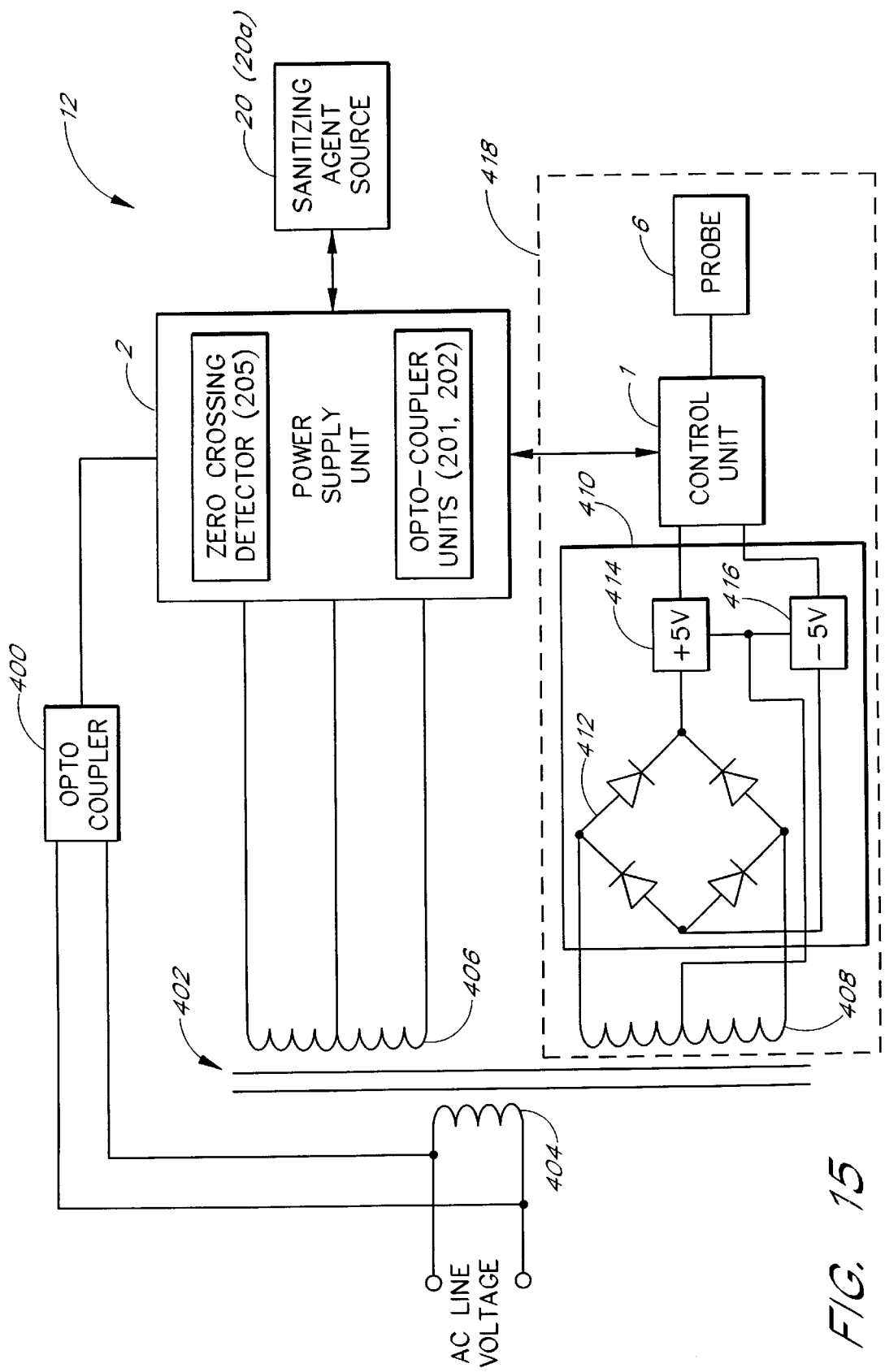
FIG. 15 is an illustration of the automatic sanitizing system including a transformer for connection to an AC line voltage.

In FIG. 15, the general architecture of the automatic sanitizing system 12 shown in FIG. 1 is illustrated to explain further the electrically isolation of the power supply unit 2 from the control unit 1. Same components have been identified by the same reference numerals.

A transformer 402 having a primary winding 404 and two secondary windings 406, 408 is connected to a 120/240 volts power line. For illustration purposes, the transformer 402 is shown to be positioned outside the power supply unit 2; however, the transformer 402 can also be positioned within the power supply unit 2. The secondary winding 406 is connected to the power supply unit 2, and the secondary winding 408 is connected to a rectifier unit 410 that comprises a rectifier 412 and two voltage regulators 414, 416. The output of the voltage regulators 414, 416 provide +5 volts and −5 volts, respectively, to the control unit 1 and to the probe 6 which is connected to the control unit 1. Electrical devices and circuits used in the preferred embodiment of the present invention, for example, the microcontroller 162, the multiplexer 194 and the reference voltage unit 160 are coupled to the +5 volts and/or −5 volts power supply outputs of the regulators 414, 416 and are grounded, as known in the art; although this is not always explicitly shown in the drawings.

The power supply unit 2 is connected to the sanitizing agent source and, via opto-coupler units 201, 202, to the control unit 1 as shown in detail in FIG. 7. Those skilled in the art will appreciate that the opto-coupler units 201, 202 may also be located with in the control unit 1. The power supply unit 2 comprises the zero crossing detector 205 (FIG. 7) which is connected to the 120/240 volts power line via a further opto-coupler 400. The zero crossing detector 205 and the detection units 208, 212 (FIG. 7) are part of a feedback circuitry.

The opto-coupler units 201, 202, 400 and the transformer 402 electrically isolate the control unit 1 and the probe 6 from the power supply unit 2 so that no common ground exists. That is, the power supply unit 2 in combination with either the electrolytic cell 20 or the dispenser 20a are electrically isolated from the control unit 1 which is coupled to probe 6. In addition, the opto-coupler units 201, 202 electrically isolate the control unit 1 and the probe 6 from a controlled device (e.g., either the electrolytic cell 20 or the dispenser 20a), whose operation the control unit 1 governs, and from the feedback circuitry, which is formed in part by the detection units 208, 212. The isolation of the control unit 1 (and the probe 6) from the power supply unit 2, the feedback circuitry, and the controlled device (e.g., the cell 20) is represented by a broken isolation line 418 around the control unit 1 and the probe 6. This isolation enhances the accuracy of the concentration level readings obtained by the amperometric sensor, and thus the performance of the system, to more precisely control and maintain the level of sanitizing agent in the water feature.

Although this invention has been described in terms of certain preferred embodiments, other embodiments that are apparent to those of ordinary skill in the art are also within the scope of this invention. Accordingly, the scope of the invention is intended to be defined by the claims that follow.

What is claimed is:

1. In combination, a water feature filled with water containing a sanitizing agent and an automatic sanitizing system comprising:

a sanitizing agent source communicating with the water in the water feature;

an amperometric sensor including a probe positioned in contact with water, wherein said probe includes a plurality of electrodes, said sensor generating an output signal indicative of the concentration of sanitizing agent in the water;

a control system receiving the signal from the sensor and operating the source at least between an active state and an inactive state depending on the concentration of the sanitizing agent in the water, whereby the concentration of the sanitizing agent in the water is automatically maintained within a preset range; and wherein said control system also controls a cleaning cycle by causing different voltages to be applied sequentially between a plurality of said electrodes of said probe.

2. The combination of claim 1, wherein the sanitizing agent includes bromine.

3. The combination of claim 2, wherein the source comprises a sanitizing agent generator which includes at least one electrolytic cell.

4. The combination of claim 3, wherein the electrolytic cell has sufficiently sized electrodes to produce bromine at a rate of approximately 1–2 grams per hour.

5. The combination of claim 2, wherein the preset range for the bromine concentration is within the range of about 2 ppm to about 6 ppm.

6. The combination of claim 5, wherein the preset range for the bromine concentration is within the range of 2.5 ppm to 3.5 ppm.

7. The combination of claim 1, wherein the water contains an electrolyte prepared by the step of adding a salt composition comprising about 50 ppm sodium bromide and at least 500 ppm sodium chloride to the water.

8. The combination of claim 7, wherein the salt composition comprises no more than about 100 ppm of sodium bromide and no more than about 1200 ppm of sodium chloride.

9. The combination of claim 3, wherein the water feature additionally comprises a water line having influent and effluent ends through which the generator communicates with the water feature.

10. The combination of claim 9, wherein the probe of the sensor is arranged with the water line and is located downstream of the generator.

11. The combination of claim 9, wherein the generator includes at least one electrolytic cell and a pump which selectively circulates water through the water line.

12. The combination of claim 11, wherein the sensor comprises a potentiostat for amperometric measurements, the potentiostat being connected to the probe, and the control system including a microcontroller coupled to the potentiostat.

13. The combination of claim 12, wherein the microcontroller is coupled to the at least one electrolytic cell and to the pump of the generator for selectively operating both the electrolytic cell and the pump.

14. The combination of claim 1, wherein the water contains an electrolyte prepared by the step of adding a salt composition comprising at least about 50 ppm halide to the water.

15. The combination of claim 1, wherein the water contains an electrolyte prepared by the step of adding a salt composition comprising 300–1000 ppm bromide as sodium bromide to the water.

16. An automatic sanitizing system comprising:

an electrolytic cell for emersion in water;

an amperometric sensor including:
 a probe positionable in contact with the water, said probe comprising a plurality of electrodes, and
 a potentiostat for amperometric measurements, the potentiostat being connected to the probe electrodes,
 wherein the sensor generates an output signal indicative of a concentration of a chemical species in the water; and a control system connected to the sensor to receive the output signal, and connected to the electrolytic cell to operate the electrolytic cell at least between active and inactive states depending on the concentration of the chemical species in the water, said control system comprising:
 a microcontroller coupled to the potentiostat to selectively receive an output signal from the potentiostat which is indicative of the concentration of the sensed chemical species, and
 a reference voltage unit that provides at least one reference voltage to the potentiostat,
 wherein the microcontroller controls the reference voltage unit to apply the at least one reference voltage to the potentiostat, the reference voltage being preset within the control system and corresponding to the particular chemical species being sensed.

17. The system of claim 16, wherein the probe includes at least a working electrode, a reference electrode and a counter electrode.

18. The system of claim 17, wherein said microcontroller is connected to an indicator and controls the indicator to display whether the measured chemical species is within a preset range.

19. The system of claim 17, wherein the potentiostat includes a follower having an input connected to the reference electrode, and an inverting summing junction having an input coupled to an output of the reference voltage unit and to an output of the follower, and an output electrically coupled to the counter electrode.

20. The system of claim 17, wherein the potentiostat applies said reference voltage between said working electrode and said reference electrode.

21. The system of claim 17, wherein the control system further controls a cleansing cycle to cause a plurality of voltages to be applied in sequence between the working electrode and the counter electrode.

22. The system of claim 21, wherein at least one of the reference voltages is a negative potential and at least one of the reference voltages is a positive potential.

23. The system of claim 22, wherein a first reference voltage of said sequence of reference voltages has a value of +1 volts and is applied for one minute, a second reference voltage of said sequence of reference voltages has a value of −80 millivolts and is applied for one minute, and a third voltage of said sequence of reference voltages has a value of +300 millivolts and is applied for one minute.

24. The system as claimed in claim 21, wherein the reference voltage unit generates a fourth reference voltage being selected to sense a chemical species other than the chemical species being sensed to control the electrolytic cell.

25. The system of claim 17, wherein the control system additionally includes a diagnostic system associated with the sensor probe for generating a signal indicative of a conductivity between the working electrode and the counter electrode, and the microcontroller receives said conductance signal and generates at least one control signal in response thereto.

26. The system of claim 25, wherein the diagnostic system includes a voltage divider with one element of the voltage divider comprising the variable impedance between the working electrode and the counter electrode.

27. The system of claim 26, wherein the diagnostic system comprises a diagnostic unit including a voltage sensor that is connected to the voltage divider and produces said conductivity signal.

28. The system of claim 26, wherein the microcontroller applies a signal with a frequency within the range between about 4 kHz and about 10 kHz to the voltage divider.

29. The system of claim 17, wherein the control system further comprises a temperature probe for measuring water temperature, said temperature probe generating a signal feedable to the microcontroller which generates at least one control signal in response at least in part thereto.

30. The system of claim 17, wherein the potentiostat and the probe of the amperometric sensor are remotely positioned relative to each other.

31. The system of claim 30, wherein a data transmission line connects the probe to the potentiostat, and the data transmission line is releasably connected to either the probe or the potentiostat.

32. The system of claim 15, further comprising an electrical pump unit, wherein the microcontroller generates a first control signal to control the electrolytic cell and a second control signal to control the electrical pump unit.

33. The system of claim 17, wherein the potentiostat includes at least two operational amplifiers, each being provided with an asymmetrical power supply by an operational amplifier sub-power supply.

34. The system of claim 17, wherein the operational amplifier sub-power supply supplies each operational amplifier with about a positive potential of about +5 volts and a negative potential in the range of about –4.2 volts and about –4.5 volts.

35. An automatic sanitizing system comprising:
an electrolytic cell for emersion in water;
an amperometric sensor including a probe positionable in contact with the water, and wherein the sensor generates an output signal indicative of a concentration of a chemical species in the water;
a control system connected to the sensor to receive the output signal, and connected to the electrolytic cell to operate the electrolytic cell at least between active and inactive states depending on the concentration of the chemical species in the water;
a power supply unit providing power for the system; and
an isolator for electrically isolating the control system from at least the power supply unit and the electrolytic cell.

36. The system of claim 35, wherein the isolator includes an opto-coupler unit positioned between control signal outputs of the microcontroller and control signal inputs of the power supply unit, and between an input of the microcontroller and an output of the power supply unit.

37. The system of claim 36, wherein the isolator further includes a transformer having a first and second secondary winding, the first secondary winding providing power for the power supply unit and the electrolytic cell, and the second secondary winding providing power for the control system and the amperometric sensor.

38. In combination, a water feature filled with water containing an electrolyte prepared by the step of adding a salt composition comprising at least about 50 ppm halide to the water, and an automatic sanitizing system comprising:
a sanitizing agent source communicating with the water feature;
an amperometric sensor including a probe comprising a plurality of electrodes positioned in contact with the water, said sensor generating an output signal indicative of the concentration of the sanitizing agent in the water; and
a control system receiving the signal from the sensor and operating the sanitizing agent source at least between an active state, in which said source increases the concentration of the sanitizing agent in the water, and an inactive state depending on the concentration of the sanitizing agent in the water, whereby the concentration of the sanitizing agent in the water is automatically maintained within a preset range; and
wherein said control system also controls a cleaning cycle by causing different voltages to be applied sequentially between a plurality of said electrodes of said probe.

39. The combination of claim 38, wherein the sanitizing agent source includes a sanitizing agent generator.

40. The combination of claim 39, wherein the generator includes at least one electrolytic cell and a pump which selectively circulates water through the electrolytic cell.

41. The combination of claim 38, wherein the sanitizing agent source includes a dispenser containing the sanitizing agent.

42. The combination of claim 38, wherein the sanitizing agent includes bromine.

43. The combination of claim 38, wherein the water contains an electrolyte prepared by the step of adding a salt composition comprising 300–1000 ppm bromide as sodium bromide to the water.

44. An automatic sanitizing system comprising:
an electrolytic cell for emersion in water;
an amperometric sensor including a probe positionable in contact with the water, the sensor generating an output signal indicative of a concentration of a chemical species in the water;
a control system connected to the sensor to receive the output signal, and connected to the electrolytic cell to operate the electrolytic cell at least between active and inactive states depending on the concentration of the chemical species in the water;
a power supply unit for the electrolytic cell, the amperometric sensor and the control system; and
an isolator which electrically isolates the control system from the power supply unit and said electrolytic cell.

45. An automatic sanitizing system comprising:
a sanitizing agent source;
an amperometric sensor including a probe positionable in contact with water, the sensor generating an output signal indicative of a concentration of a sanitizing agent in the water, the probe includes at least a working electrode, a reference electrode and a counter electrode, and the sensor includes a potentiostat for amperometric measurements, the potentiostat being connected to the probe electrodes and including a follower having an input connected to the reference electrode, and an inverting summing junction having an input coupled to an output of the reference voltage unit and to an output of the follower, and an output electrically coupled to the counter electrode; and a control system connected to the sensor to receive the output signal, and connected to the sanitizing agent source to operate the sanitizing agent source at least between active and inactive states depending on the concentration of the sanitizing agent in the water, wherein in the active state the sanitizing agent source is adapted to increase the concentration of the sanitizing agent in the water, the control system including a microcontroller coupled to the potentiostat to selectively receive the output signal from the potentiostat which is indicative of the concentration of the sensed chemical species, the control system further comprising a reference voltage unit that provides at least one reference voltage to the potentiostat.

46. The system of claim 45, wherein the sanitizing agent source includes a sanitizing agent generator.

47. The system of claim 45, wherein the microcontroller controls the reference voltage unit to apply the at least one reference voltage to the potentiostat, the voltage value being preset within the control system and corresponding to the particular chemical species being sensed.

48. The system of claim 47, wherein the potentiostat applies said reference voltage between said working electrode and said reference electrode.

49. The system of claim 48, wherein the control system further controls a cleansing cycle to cause different voltages to be applied in sequence between the working electrode and the counter electrode.

50. The system of claim 49, wherein at least one of the reference voltages is a negative potential and at least one of the reference voltages is a positive potential.

51. The system of claim 50, wherein a first reference voltage of said sequence of reference voltages has a value of +1 volts and is applied for one minute, a second reference voltage of said sequence of reference voltages has a value of −0.08 volts and is applied for one minute, and a third voltage of said sequence of reference voltages has a value of +300 millivolts and is applied for one minute.

52. In combination, a water feature filled with water containing a sanitizing agent and an automatic sanitizing system comprising:

a sanitizing agent generator communicating with the water;

an amperometric sensor including a probe positioned in contact with water, said sensor generating an output signal indicative of the concentration of sanitizing agent in the water;

a control system receiving the signal from the sensor and operating the generator at least between an active state and an inactive state depending on the concentration of the sanitizing agent in the water, whereby the concentration of the sanitizing agent in the water is automatically maintained within a preset range;

a power supply unit for the sanitizing agent generator, the amperometric sensor, and the control system; and an isolator which electrically isolates the control system from the power supply unit and the sanitizing agent generator.

53. The combination of claim 52, wherein the sanitizing agent includes bromine.

54. The combination of claim 53, wherein the sanitizing agent generator includes at least one electrolytic cell.

55. The combination of claim 54, wherein the electrolytic cell has sufficiently sized electrodes to produce bromine at a rate of approximately 1–2 grams per hour.

56. The combination of claim 53, wherein the preset range for the bromine concentration is within the range of about 2 ppm to about 6 ppm.

57. The combination of claim 56, wherein the preset range for the bromine concentration is within the range of 2.5 ppm to 3.5 ppm.

58. The combination of claim 52, wherein the water contains an electrolyte prepared by the step of adding a salt composition comprising about 50 ppm halide to the water.

59. The combination of claim 52, wherein the water contains an electrolyte prepared by the step of adding a salt composition comprising about 300–1000 ppm bromide as sodium bromide to the water.

60. The combination of claim 52, wherein the water feature additionally comprises a water line having influent and effluent ends that provide fluid communication with the water feature, said generator disposed relative to the water line such that fluid flow through said line is introduced into said generator.

61. The combination of claim 60, wherein the probe of the sensor is in the water line downstream of the generator.

62. The combination of claim 60, wherein the generator includes at least one electrolytic cell and a pump which selectively circulates water through the water line.

63. An automatic sanitizing system comprising:

an electrolytic cell for emersion in water;

an amperometric sensor including a probe positionable in contact with the water, the sensor generating an output signal indicative of a concentration of a chemical species in the water; and a control system connected to the sensor to receive the output signal, and connected to the electrolytic cell to operate the electrolytic cell at least between active and inactive states depending on the concentration of the chemical species in the water;

wherein the probe includes at least a working electrode, a reference electrode and a counter electrode, and the sensor includes a potentiostat for amperometric measurements, the potentiostat being connected to the probe electrodes, and the control system including a microcontroller coupled to the potentiostat to selectively receive an output signal from the potentiostat which is indicative of the concentration of the sensed chemical species; and wherein the control system additionally comprises a reference voltage unit that provides at least one reference voltage feedable to the potentiostat; and wherein the potentiostat includes an inverter having an output connected to the counter electrode, a follower having an input connected to the reference electrode, and an inverting summing junction having an input coupled to an output of the reference voltage unit and to an output of the follower, and an output connected to an input of the inverter.

64. An automatic sanitizing system comprising:

an electrolytic cell for emersion in water;

an amperometric sensor including a probe positionable in contact with the water, the sensor generating an output signal indicative of a concentration of a chemical species in the water; and a control system connected to the sensor to receive the output signal, and connected to the electrolytic cell to operate the electrolytic cell at least between active and inactive states depending on the concentration of the chemical species in the water;

wherein the probe includes at least a working electrode, a reference electrode and a counter electrode, and the sensor includes a potentiostat for amperometric measurements, the potentiostat being connected to the probe electrodes, and the control system including a microcontroller coupled to the potentiostat to selectively receive an output signal from the potentiostat which is indicative of the concentration of the sensed chemical species; and wherein the control system additionally comprises a reference voltage unit that provides at least one reference voltage feedable to the potentiostat; and wherein the microcontroller controls the reference voltage unit to apply the at least one reference voltage to the potentiostat, the voltage value being preset within the control system and corresponding to the particular chemical species being sensed.

65. The system of claim 64, wherein the potentiostat applies said reference voltage between said working electrode and said reference electrode.

66. The system of claim 64, wherein the control system further controls the reference voltage unit in a cleansing cycle to cause said reference voltage unit to output a sequence of three different reference voltages, said sequence of reference voltages applied to the potentiostat to produce said sequence of voltages between the working electrode and the counter electrode.

67. The system of claim 66, wherein at least one of the reference voltages is a negative potential and at least one of the reference voltages is a positive potential.

68. The system of claim 67, wherein a first reference voltage of said sequence of reference voltages has a value of +1 volts and is applied for one minute, a second reference voltage of said sequence of reference voltages has a value of −80 millivolts and is applied for one minute, and a third voltage of said sequence of reference voltages has a value of +300 millivolts and is applied for one minute.

69. The system as claimed in claim 66, wherein the reference voltage unit generates a fourth reference voltage being selected to sense a chemical species other than the chemical species being sensed to control the electrolytic cell.

70. An automatic sanitizing system comprising:

an electrolytic cell for emersion in water;

an amperometric sensor including a probe positionable in contact with the water, the sensor generating an output signal indicative of a concentration of a chemical species in the water; and a control system connected to the sensor to receive the output signal, and connected to the electrolytic cell to operate the electrolytic cell at least between active and inactive states depending on the concentration of the chemical species in the water;

wherein the probe includes at least a working electrode, a reference electrode and a counter electrode, and the sensor includes a potentiostat for amperometric measurements, the potentiostat being connected to the probe electrodes, and the control system including a microcontroller coupled to the potentiostat to selectively receive an output signal from the potentiostat which is indicative of the concentration of the sensed chemical species; and wherein the control system additionally includes a diagnostic system associated with the sensor probe for generating a signal indicative of a conductivity between the working electrode and the reference electrode, and the microcontroller receives said conductance signal and generates at least one control signal in response thereto; and wherein the diagnostic system includes a voltage divider with one element of the voltage divider comprising the variable impedance between the working electrode and the reference electrode.

71. The system of claim 70, wherein the diagnostic system comprises a diagnostic unit including a voltage sensor that is connected to the voltage divider and produces said conductivity signal.

72. The system of claim 70, wherein the microcontroller applies a signal with a frequency within the range between about 4 kHz and about 10 kHz to the voltage divider.

73. An automatic sanitizing system comprising:

an electrolytic cell for emersion in water;

an amperometric sensor including a probe positionable in contact with the water, the sensor generating an output signal indicative of a concentration of a chemical species in the water;

a control system connected to the sensor to receive the output signal, and connected to the electrolytic cell to operate the electrolytic cell at least between active and inactive states depending on the concentration of the chemical species in the water;

a power supply unit providing power for the system; and an isolator for electrically isolating the control system from at least the power supply unit and the electrolytic cell;

wherein the probe includes at least a working electrode, a reference electrode and a counter electrode, and the sensor includes a potentiostat for amperometric measurements, the potentiostat being connected to the probe electrodes, and the control system including a microcontroller coupled to the potentiostat to selectively receive an output signal from the potentiostat which is indicative of the concentration of the sensed chemical species.

74. The system of claim 73, wherein the isolator includes an opto-coupler unit positioned between control signal outputs of the microcontroller and control signal inputs of the power supply unit, and between an input of the microcontroller and an output of the power supply unit.

75. The system of claim 74, wherein the isolator further includes a transformer having a first and second secondary winding, the first secondary winding providing power for the power supply unit and the electrolytic cell, and the second secondary winding providing power for the control system and the amperometric sensor.

76. An automatic sanitizing system comprising:

a sanitizing agent source;

an amperometric sensor including a probe positionable in contact with water, the sensor generating an output signal indicative of a concentration of a sanitizing agent in the water, the probe includes at least a working electrode, a reference electrode and a counter electrode, and the sensor includes a potentiostat for amperometric measurements, the potentiostat being connected to the probe electrodes and including at least two operational amplifiers, each being provided with an asymmetrical power supply by an operational amplifier sub-power supply; and a control system connected to the sensor to receive the output signal, and connected to the sanitizing agent source to operate the sanitizing agent source at least between active and inactive states depending on the concentration of the sanitizing agent in the water, wherein in the active state the sanitizing agent source is adapted to increase the concentration of the sanitizing agent in the water, the control system including a microcontroller coupled to the potentiostat to selectively receive the output signal from the potentiostat which is indicative of the concentration of the sensed chemical species;

wherein the sanitizing agent source includes a sanitizing agent generator; and wherein the control system additionally comprises a reference voltage unit that provides at least one reference voltage feedable to the potentiostat.

77. The system of claim 76, wherein the potentiostat includes an inverter having an output connected to the counter electrode, a follower having an input connected to the reference electrode, and an inverting summing junction having an input coupled to an output of the reference voltage unit and to an output of the follower, and an output connected to an input of the inverter.

78. The system of claim 76, wherein the microcontroller controls the reference voltage unit to apply the at least one reference voltage to the potentiostat, the voltage value being preset within the control system and corresponding to the particular chemical species being sensed.

79. The system of claim 78, wherein the potentiostat applies said reference voltage between said working electrode and said reference electrode.

80. The system of claim 79, wherein the control system further controls the reference voltage unit in a cleansing cycle to cause said reference voltage unit to output a sequence of three different reference voltages, said sequence of reference voltages applied to the potentiostat to produce said sequence of voltages between the working electrode and the counter electrode.

81. The system of claim 80, wherein at least one of the reference voltages is a negative potential and at least one of the reference voltages is a positive potential.

82. The system of claim 81, wherein a first reference voltage of said sequence of reference voltages has a value of +1 volts and is applied for one minute, a second reference voltage of said sequence of reference voltages has a value of −0.08 volts and is applied for one minute, and a third voltage of said sequence of reference voltages has a value of +300 millivolts and is applied for one minute.

* * * * *